United States Patent
Cho et al.

(10) Patent No.: US 10,598,580 B2
(45) Date of Patent: Mar. 24, 2020

(54) VISCOMETERS AND METHODS OF MEASURING LIQUID VISCOSITY

(71) Applicant: Health Onvector Inc., Camden, NJ (US)

(72) Inventors: Daniel J. Cho, Chesterbrook, PA (US); Joseph Weidman, Mohnton, PA (US)

(73) Assignee: HEALTH ONVECTOR INC, Camden, NJ (US)

( * ) Notice: Subject to any disclaimer, the term of this patent is extended or adjusted under 35 U.S.C. 154(b) by 157 days.

(21) Appl. No.: 15/535,738

(22) PCT Filed: Dec. 21, 2015

(86) PCT No.: PCT/US2015/067079
§ 371 (c)(1),
(2) Date: Jun. 14, 2017

(87) PCT Pub. No.: WO2016/100969
PCT Pub. Date: Jun. 23, 2016

(65) Prior Publication Data
US 2018/0356325 A1    Dec. 13, 2018

Related U.S. Application Data

(60) Provisional application No. 62/094,348, filed on Dec. 19, 2014.

(51) Int. Cl.
*G01N 11/06* (2006.01)
*G01N 11/08* (2006.01)
*G01N 13/02* (2006.01)

(52) U.S. Cl.
CPC .............. *G01N 11/06* (2013.01); *G01N 11/08* (2013.01); *G01N 13/02* (2013.01); *G01N 2013/0283* (2013.01)

(58) Field of Classification Search
CPC ........ G01N 11/06; G01N 11/08; G01N 13/02; G01N 2013/0283
See application file for complete search history.

(56) References Cited

U.S. PATENT DOCUMENTS

| 2,829,515 | A | * | 4/1958 | Johnson | G01N 15/088 73/38 |
| 3,071,961 | A | * | 1/1963 | Heigl | G01N 11/06 73/54.08 |
| 4,858,127 | A | * | 8/1989 | Kron | G01N 11/00 73/54.09 |
| 5,057,078 | A | | 10/1991 | Foote | |

(Continued)

FOREIGN PATENT DOCUMENTS

EP    0270616    6/1988

OTHER PUBLICATIONS

Goncalves, F. A. et al. Surface-tension effects in suspended-level capillary viscometers. International journal of thermophysics, 1991, 12.6: 1013-1028.(Dec. 31, 1991).

(Continued)

*Primary Examiner* — Francis C Gray
(74) *Attorney, Agent, or Firm* — Riverside Law LLP

(57) ABSTRACT

The present invention relates to the field of liquid viscosity measurement using a capillary tube. The invention pertains to novel methods that use surface tension driven flow for the measurement of viscosity of a liquid over a range of shear rates.

6 Claims, 16 Drawing Sheets

(56) References Cited

U.S. PATENT DOCUMENTS

| | | | | |
|---|---|---|---|---|
| 5,080,865 | A | * | 1/1992 | Leiner ................... G01N 1/28 204/401 |
| 5,347,851 | A | * | 9/1994 | Grudzien, Jr. ........ G01L 9/0077 374/56 |
| 5,505,831 | A | * | 4/1996 | Liao ................. G01N 27/44743 204/451 |
| 5,597,468 | A | * | 1/1997 | Lauer ............... G01N 27/44743 204/453 |
| 5,665,311 | A | * | 9/1997 | Gorog ............... G01N 33/4905 422/73 |
| 6,039,078 | A | | 3/2000 | Tamari |
| 6,402,703 | B1 | | 6/2002 | Kensey |
| 6,450,974 | B1 | | 9/2002 | Kim |
| 6,484,566 | B1 | * | 11/2002 | Shin ................... A61B 5/02035 324/71.1 |
| 6,692,437 | B2 | | 2/2004 | Kensey |
| 7,600,416 | B2 | | 10/2009 | Lin |
| 2003/0158500 | A1 | * | 8/2003 | Kensey ............. A61B 5/02035 600/573 |
| 2009/0205410 | A1 | | 8/2009 | Lin |

OTHER PUBLICATIONS

B. Munson, T. H. Okiishi, W. Huebsch, and D. Young, "Fundamentals of Fluid Mechanics," ed: New York: John Wiley & Sons Inc, 2013.

S. Kaya and A. R. Tekin, "The effect of salep content on the rheological characteristics of a typical ice-cream mix," Journal of Food Engineering, vol. 47, pp. 59-62, 2001.

S. Kim, Y. Cho, W. Hogenauer, and K. Kensey, "A method of isolating surface tension and yield stress effects in a U-shaped scanning capillary-tube viscometer using a Casson model" Journal of Non-Newtonian Fluid Mechanics, vol. 103, pp. 205-219, 2002.

J. Canny, "A computational approach to edge detection," Pattern Analysis and Machine Intelligence, IEEE Transactions on, pp. 679-698, 1986.

E. Nadernejad, S. Sharifzadeh, and H. Hassanpour, "Edge detection techniques: evaluations and comparison," Applied Mathematical Sciences, vol. 2, pp. 1507-1520, 2008.

N. R. Pal and S. K. Pal, "A review on image segmentation techniques," Pattern recognition, vol. 26, pp. 1277-1294, 1993.

S. Middleman, Flow of high polymers; continuum and molecular rheology. New York, NY: John Wiley & Sons, Inc., 1968.

* cited by examiner

VISCOMETERS AND METHODS OF MEASURING LIQUID VISCOSITY

CROSS-REFERENCE TO RELATED APPLICATIONS

This application claims priority to PCT International Patent Application No. PCT/US 15/67079, filed on Dec. 21, 2015, which claims priority to U.S. Provisional Patent Application No. 62/094,348, filed on Dec. 19, 2014, both of which are incorporated by reference herein in their entireties.

BACKGROUND OF THE INVENTION

When fluid flows through a tube or pipe, there is friction between the moving fluid and pipe wall. The amount of friction is primarily due to the viscosity of the fluid (B. Munson, T. H. Okiishi, W. Huebsch, and D. Young, "Fundamentals of Fluid Mechanics," ed: New York: John Wiley & Sons Inc, 2013). In fluid dynamics, the viscosity µ is defined as the proportionality constant between wall shear stress $\tau_{wall}$ and wall shear rate $\dot{\gamma}_{wall}$ (B. Munson, T. H. Okiishi, W. Huebsch, and D. Young, "Fundamentals of Fluid Mechanics," ed: New York: John Wiley & Sons Inc, 2013).

$$\tau_{wall} = \mu \cdot [\dot{\gamma}_{wall}] \qquad \text{Eq. (1)}$$

where the wall shear stress [N/m²] is a tangential or frictional force per unit area, and the wall shear rate [s⁻¹] is a velocity gradient at pipe wall, i.e., $[du/dr]_{wall}$. Note that u or u(r) indicates the axial flow velocity profile in pipe flow, and r represents the radial coordinate in the pipe flow. The wall shear rate can be conceptually described as the ratio of the mean flow velocity V to pipe diameter d, i.e., ~V/d. For Newtonian fluids, the wall shear rate is analytically determined as 8 V/d in a laminar flow in a circular pipe (B. Munson, T. H. Okiishi, W. Huebsch, and D. Young, "Fundamentals of Fluid Mechanics," ed: New York: John Wiley & Sons Inc, 2013).

The viscosities of water and air do not vary with shear rate, whereas the viscosities of fluids such as paint, tomato ketchup, blood, synthetic engine oil, and polymer solutions vary with the shear rate. The liquids whose visocisties are independent of shear rate are referred to as Newtonian fluids, while the liquids whose viscosities are dependent on the shear rate are described as non-Newtonian fluids (B. Munson, T. H. Okiishi, W. Huebsch, and D. Young, "Fundamentals of Fluid Mechanics," ed: New York: John Wiley & Sons Inc, 2013).

In the field of engineering, the viscosity of non-Newtonian fluids (e.g. synthetic oils and polymer solutions) is usually measured with a rotating-type viscometer such as the Brookfield cone and plate viscometer (S. Kaya and A. R. Tekin, "The effect of salep content on the rheological characteristics of a typical ice-cream mix," Journal of Food Engineering, vol. 47, pp. 59-62, 2001). However, it is not practical to use such rotating viscometers for blood viscosity measurements in clinical settings because the test section in rotating viscometers must be manually cleaned after each viscosity test, a procedure that is unsafe to the operator due to the potential risk of making contact with contaminated blood.

The prior art describes the use of a U-shaped tube assembly, where a capillary tube is positioned horizontally between two vertical tubes (K. Kensey and Y. Cho, "Method for determining the viscosity of an adulterated blood sample over plural shear rates," 2004; K. Kensey, W. N. Hogenauer, S. Kim, and Y. Cho, "Dual riser/single capillary viscometer," 2002). This method presents capillary-based viscometry capable of measuring viscosity across a range of shear rates using a single sweeping scan. The U-shaped tube assembly in this prior art is disposable, enabling the technician or operator to avoid direct contact with blood. While this prior art provided improvements over earlier viscometer methods, it has a number of profound limitations that limit its functionality, accuracy, and practical use.

In a case where a liquid having an unknown viscosity fills the left-side vertical tube first to a predetermined height, the liquid begins to fall at the beginning of the test by gravity, moving through the capillary tube, and rising in the right-side vertical tube. In an idealized scenario, the liquid levels in the two vertical tubes become equal as time goes to infinity (i.e. the end of the test). However, due to the difference in the surface tension in the two vertical tubes, the left and right liquid levels do not perfectly equilibrate, even at t=infinity. The reason is as follows: as the liquid falls in the left-side vertical tube, the inner wall of the vertical tube is fully wet during the operation of the test. On the other hand, as the liquid rises in the right vertical tube, the inner wall of the right vertical tube remains fully dry prior to and at the interface of liquid movement during operation of the test. Accordingly, the surface tension in the liquid-falling tube is consistently larger than in the liquid-rising tube because the magnitude of the surface tension in a wet tube is significantly greater than that in a dry tube (B. Munson, T. H. Okiishi, W. Huebsch, and D. Young, "Fundamentals of Fluid Mechanics," ed: New York: John Wiley & Sons Inc, 2013).

Accordingly, the liquid level in the liquid-falling tube is significantly higher than that in the liquid-rising tube at the end of the test. This liquid height difference is caused by the different surface tensions in the two vertical tubes and can affect the accuracy of viscosity measurement of the liquid near the end of the test, especially at low-shear ranges of less than 10 s⁻¹. Since the difference in the surface tensions in the two vertical tubes could not be resolved in the prior art, the surface tension term was numerically isolated in the calculation of viscosity in S. Kim, Y. Cho, W. Hogenauer, and K. Kensey, "A method of isolating surface tension and yield stress effects in a U-shaped scanning capillary-tube viscometer using a Casson model" Journal of Non-Newtonian Fluid Mechanics, vol. 103, pp. 205-219, 2002. More specifically, the Casson model was used to relate the shear stress and shear rate using two unknown constants: Casson constant k and yield stress $\tau_y$. The surface tension term was added as the third unknown constant, which had to be numerically determined in the minimization algorithm (i.e., minimizing the sum of the error in the curve fitting of experimental data of the liquid level variation over time). While this prior art describes a capillary-based method for measuring viscosity across multiple shear rates, there is still a need to measure more accurately the surface tension of the liquid.

Another limitation of the prior art is associated with the liquid-falling vertical tube. In the clinical case of hyperviscosity syndrome, common in polycythemias, multiple myeloma, leukemia, monoclonal gammopathies such as Waldenström macroglobulinemia, sickle cell anemia, and sepsis, whole blood often becomes very sticky. As blood falls in the liquid-falling vertical tube, a small droplet of blood can stick to the vertical wall, leaving a streak of blood, which becomes a significant source of error in the viscosity measurement.

Furthermore, the prior art utilized a gravity-driven flow in a U-shaped tube, where blood falls from one vertical tube by gravity, passes through the capillary tube, and then rises in another vertical tube. Blood moves through the capillary tube by the height difference between the two vertical tubes. In clinical cases of hyperviscosity syndrome (as well as with other very thick liquids such as yogurt, grease, and slurry of suspended particles), gravity alone cannot push the liquid through the capillary tube of the viscometer described in these prior arts because of increased friction caused by the thick liquid and small diameter of the capillary tube (i.e., less than 0.8 cm). Hence, the method in the prior art cannot measure the viscosity of thick liquids using the U-shaped tube beyond a certain threshold viscosity.

In summary, the prior art utilizes a gravity-driven flow in a U-shaped tube, where changes in the liquid height over time within the two vertical tubes are measured. The liquid viscosity is determined from the first derivative (i.e., slope) dh(t)/dt of the height change h(t). The procedure of taking the first derivative of the height change for multiple time points is calculation-intensive, requiring a microprocessor for the data reduction process. Furthermore, the need to calculate the first derivative significantly increases the potential for error in the viscosity measurement, because the liquid height changes in the two vertical tubes are naturally punctuated and are often not smooth. For example, a small pause of liquid motion or small sudden drop will be magnified in the first derivative of the height change.

There is a need in the art for an improved viscometers and methods for more accurately measuring and calculating liquid viscosity. The present invention meets this need.

SUMMARY OF THE INVENTION

The present invention provides improved methods for calculating liquid viscosity and devices for implementing the same. The methods improve accuracy by basing viscosity calculations on measurements of liquid surface tension.

In one embodiment, a viscosity measuring device includes a reservoir; a capillary tube having a first end and a second end, the first end fluidly connected to the reservoir, the second end extending away from the reservoir; a connecting tube having a first end, a second end, and a flow control mechanism therebetween, wherein the first end is fluidly connected to the second end of the capillary tube; and a transparent tube having a first end and a second end and oriented vertically from end to end, wherein the first end is fluidly connected to the second end of the connecting tube and the second end is exposed to atmospheric pressure at a height above the reservoir; where the internal diameter of the capillary tube is smaller than the internal diameter of the transparent tube. In one embodiment, the device includes a plunger and a dead weight dimensioned to fit within the reservoir. In one embodiment, the flow-control mechanism is selected from the group consisting of a valve, a slide lock, and a tube-restricting clip. In one embodiment, the device includes a linear light source and a linear series of photodiodes positioned on opposite sides of the transparent vertical tube, wherein the linear light source shines light through the transparent vertical tube that is detected by the linear series of photodiodes, and wherein a liquid sample moving through the transparent vertical tube is tracked based on the occlusion of light as detected by the linear series of photodiodes. In one embodiment, the device includes a contact image sensor positioned adjacent and parallel to the transparent vertical tube, wherein a liquid sample moving through the transparent vertical tube is tracked by the contact image sensor. In one embodiment, the device includes a camera system, wherein a liquid sample moving through the transparent vertical tube is tracked by the camera system. In one embodiment, the device includes a temperature regulating enclosure containing at least the reservoir, capillary tube, connecting tube and the transparent tube. In one embodiment, a method of testing a liquid sample using the device includes the steps of: loading a liquid sample into the reservoir; opening the flow-control mechanism; recording the start time point when the liquid sample flows past the horizontal reference line in the transparent vertical tube; recording the end time point when the liquid sample height in the transparent vertical tube matches the liquid sample height in the reservoir; and recording the height of the liquid sample in the transparent vertical tube and the reservoir at the end time point. In one embodiment, a method of calculating viscosity p of a liquid sample uses the device and the equation:

$$\mu = \left[\frac{d^2}{32L}\right]\frac{\Delta P_c}{V_c}$$

wherein
d=inner diameter of the capillary tube;
L=length of the capillary tube;
$\Delta P_c$=pressure drop across the capillary tube; and
$V_c$=mean flow velocity at the capillary tube.

In one embodiment, a viscosity measuring device includes: a reservoir elevated above a horizontal reference line; a capillary tube aligned along the horizontal reference line having a first end and a second end, the first end fluidly connected to the reservoir, a transparent vertical tube having a first end and a second end, the first end fluidly connected to the second end of the capillary tube above the horizontal reference line and the second end fluidly connected to a pump and valve; where a liquid sample deposited into the reservoir is able to be drawn into the capillary tube and the vertical tube by a vacuum force generated by the pump, and wherein the vacuum force may be released by opening the valve. In one embodiment, the device includes a means for tracking liquid sample moving through the transparent vertical tube selected from the group consisting of: a linear light source and photodiode array; a contact image sensor; and a camera system. In one embodiment, the device includes a controller for controlling the pump and the valve. In one embodiment, the controller receives one or more inputs from a sensor. In one embodiment, a method of testing a liquid sample using the device includes the steps of: loading a liquid sample into the reservoir, drawing the liquid sample into the transparent vertical tube to a predetermined height using the vacuum pump and closing the valve; opening the valve and recording the start time point at the time of opening; recording the end time point when the liquid sample ceases to flow; and recording the height of the liquid sample in the transparent vertical tube and the reservoir at the end time point.

In one embodiment, a viscosity measuring device includes a syringe fluidly connected to a valve; a first reservoir having a first end and a second end, the first end fluidly connected to the valve; a capillary tube having a first end and a second end, the first end fluidly connected to the first reservoir; a second reservoir having a first end and a second end, the first end fluidly connected to the second end of the capillary tube; and an air chamber comprising a pressure transducer, the air chamber fluidly connected to the second end of the second reservoir, where the syringe and valve are removable, and wherein a liquid sample deposited into the first reservoir can be displaced into the second reservoir by air displaced by the syringe to create a pressure in the air chamber, and wherein the pressure may be released by opening the valve. In one embodiment, the syringe includes a plunger that is at least partially lockable. In one embodiment, the first reservoir, capillary tube, second reservoir, and fluid connections may be contained within a single module. In one embodiment, the module is disposable. In one embodiment, a method of testing a liquid sample using the device includes the steps of loading a liquid sample into the first reservoir; attaching the syringe and the valve to the first reservoir with the syringe being at least partially drawn and the valve closed; applying a compression force to the syringe to displace the liquid sample into the second reservoir and to introduce a pressure into the air chamber, opening the valve and recording the start time point at the time of opening; and recording the end time point when the pressure in the air chamber reaches atmospheric pressure. In one embodiment, a method of calculating viscosity p of a liquid sample uses the device and the equation:

$$\mu = \left(\frac{A_c \cdot d^2}{32 \cdot L \cdot VOL_2(t)}\right)\left[\frac{(P_2(t) - P_1 - \Delta P_{in}) \cdot P_2(t)}{\left(\frac{dP_2(t)}{dt}\right)}\right]$$

wherein
$A_c$=cross-sectional area of the capillary tube;
d=inner diameter of the capillary tube;
L=length of the capillary tube;
$VOL_2(t)$=volume of air in the air chamber;
$P_2(t)$=pressure in the air chamber; and
$P_1$=atmospheric pressure.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

The present invention relates to the field of liquid viscosity measurement using devices including a capillary tube. The invention pertains to novel devices, systems and methods that use surface tension driven flow for the measurement of viscosity of a liquid over a range of shear rates.
Definitions It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Viscosity Measuring Devices

Figure 1:
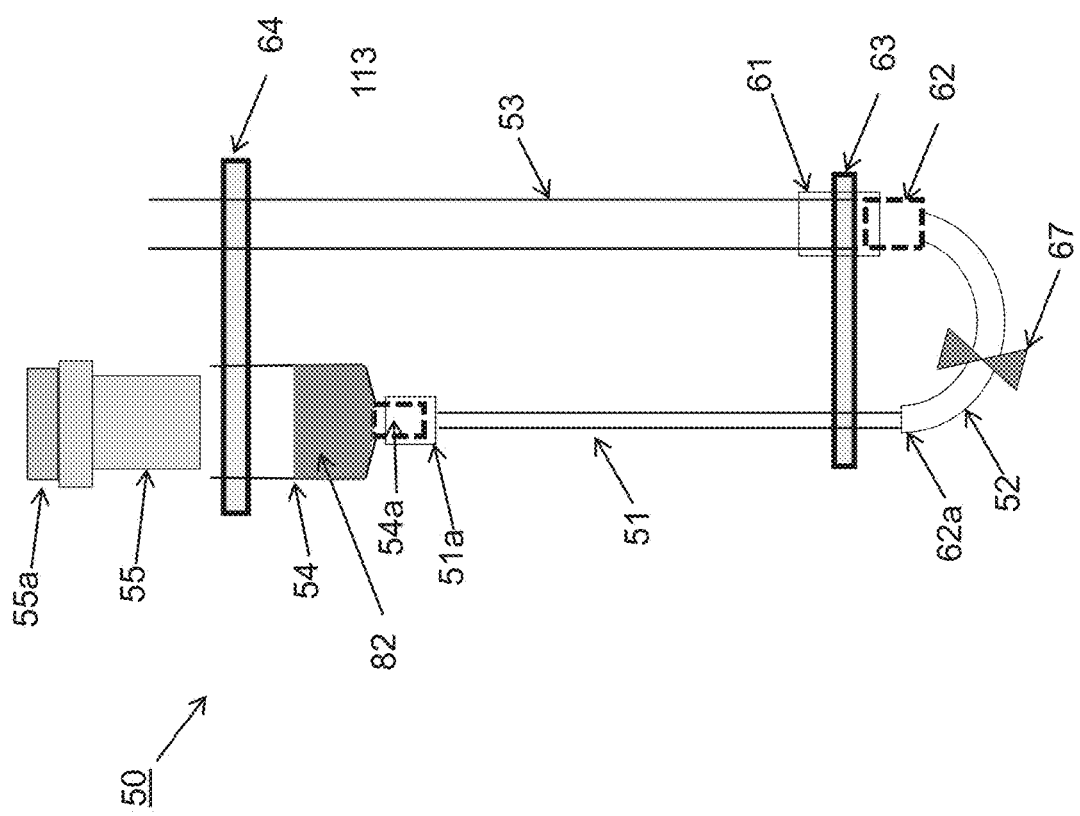
FIG. 1 depicts a diagram of an exemplary viscosity measuring device of the present invention.

Referring now to FIG. 1, an exemplary viscosity measuring device 50 is depicted. Viscosity measuring device 50 measures the viscosity of liquid sample 82 using a disposable U-shaped tube, including liquid reservoir 54 with luer connection 54a, capillary tube 51 with luer connection 51a, elbow tube 52 with luer connection 62, and transparent vertical tube 53, wherein liquid height change is measured over time. In various embodiments, elbow tube 52 comprises a flexible material. Flow-control mechanism 67 controls the flow of liquid sample 82 through elbow tube 52. Flow-control mechanism 67 can be any suitable mechanism, such as a valve, a slide lock, a tube-restricting clip, and the like. Elbow tube 52 has a first end 62a connected to capillary tube 51 and a second end 62 connected to luer connection 61. In certain embodiments, the inside diameter of the capillary tube 51 is in the range of 0.4-1.0 mm, while the length of the capillary tube 51 is in the range of 50-100 mm. In certain embodiments, the inside diameter of the transparent vertical tube 53 is in the range of 2-3 mm, and the length of the vertical tube 53 is in the range of 50-120 mm. In certain embodiments, the size of the liquid reservoir 54 is in the range of 1-3 ml as the actual liquid sample volume 82 for viscosity test will be in the range of 1.5 ml.

Upper plane 64 and lower plane 63 mechanically secure the components of device 50. In some embodiments, upper plane 64 and lower plane 63 may secure a plurality of components, such that a plurality of devices 50 are held for high throughput testing.

Figure 2:
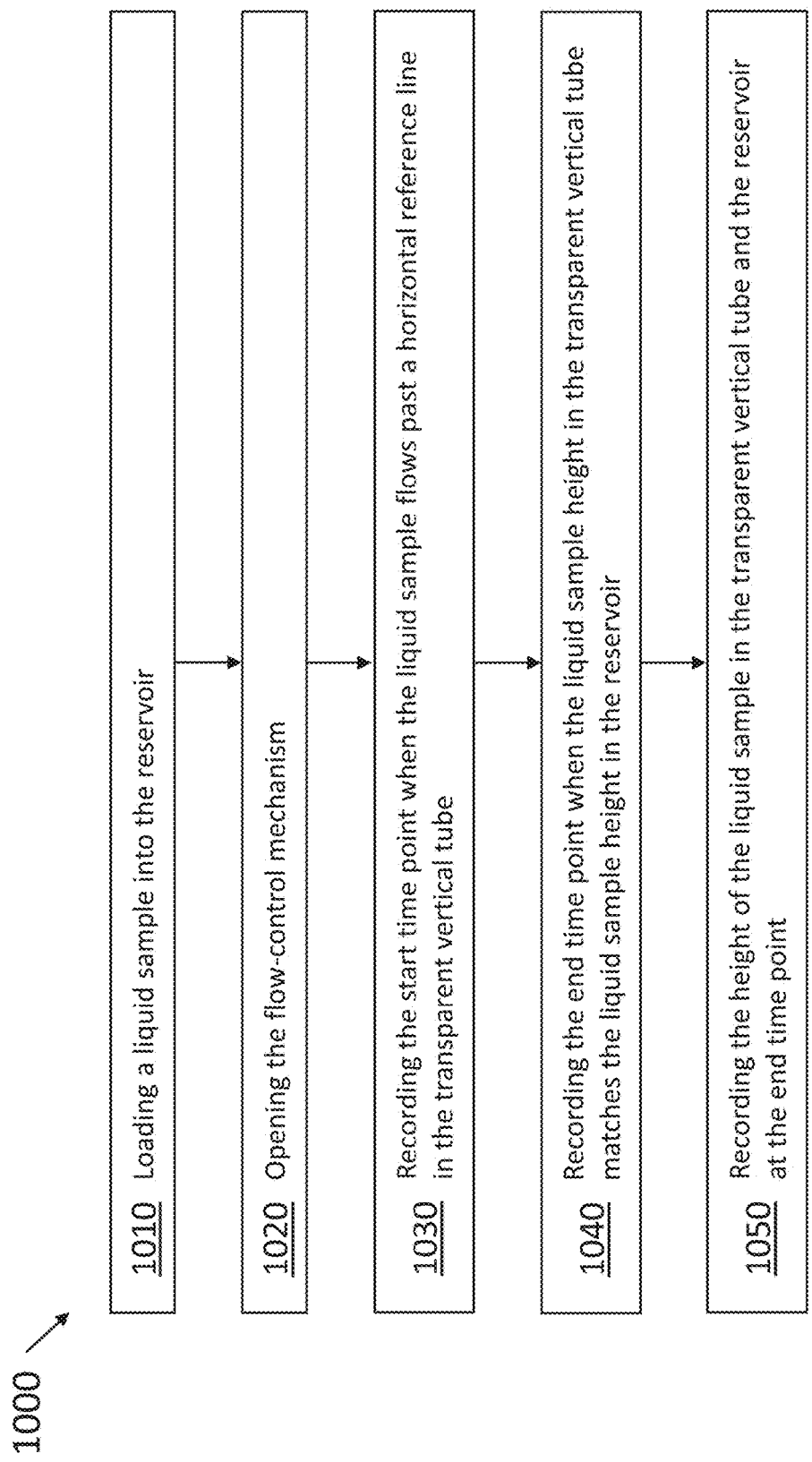
FIG. 2 is a flowchart depicting an exemplary method of using a viscosity measuring device of FIG. 1.

Referring now to FIG. 2 and with continued reference to components of FIG. 1, an exemplary method 1000 of using viscosity measuring devices, such as device 50, is depicted. Flow-control mechanism 67 is kept closed prior to initiating a viscosity test. In step 1010, a predetermined volume of liquid sample 82 is first introduced into liquid reservoir 54. In step 1020, flow-control mechanism 67 is opened, and liquid sample 82 begins to flow through capillary tube 51 and elbow tube 52 by gravity. As liquid sample 82 flows through elbow tube 52 and into transparent liquid-rising vertical tube 53, the flow rate slows with time. In step 1030, the start time point when liquid sample 82 flows past a horizontal reference line in vertical tube 53 is recorded for use in the viscosity calculations described elsewhere herein.

The viscosity test ends when the liquid sample height in vertical tube 53 equilibrates with the liquid level in reservoir 54 and capillary tube 51. In step 1040, the end time point is recorded when the liquid sample height in vertical tube 53 matches the liquid level in reservoir 54. In step 1050, the liquid level height in vertical tube 53 and reservoir 54 are recorded.

In some embodiments, device 50 further comprises plunger 55 and dead weight 55a to push very thick liquid samples. Plunger 55 and dead weight 55a are useful when gravity alone is insufficient to induce flow through capillary tube 51. In other embodiments, any fluid pumping or driving mechanism may be used to induce flow through capillary tube 51.

The viscosity measuring devices of the present invention may incorporate any suitable means for tracking and measuring the flow of a liquid sample through the devices during a viscosity test. For example, a viscosity measuring device may comprise manual means for tracking and measuring liquid sample flow, such as by volume markings on the device, wherein an operator observes the rate of flow based on the movement of liquid sample relative to the volume markings over time. In other embodiments, a viscosity measuring device may comprise machine-based means for tracking and measuring liquid sample flow, such as by photodiode systems, contact image sensor systems, camera systems, and the like.

Figure 3:
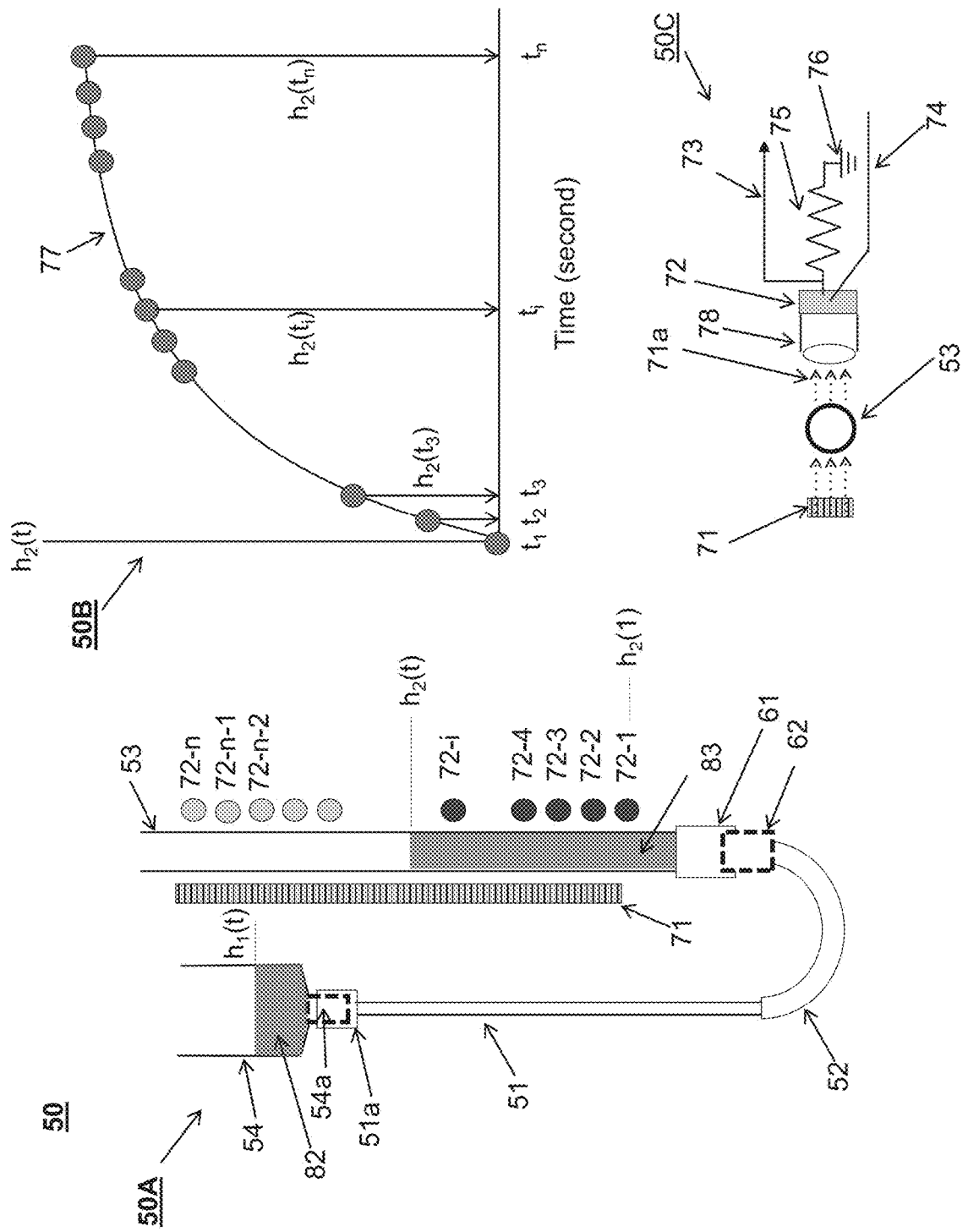
FIG. 3 depicts a diagram of a linear light source and multiple photodiodes for transient liquid level measurements in the vertical tube of an exemplary viscosity measuring device of the present invention.

Referring now to FIG. 3, an exemplary viscosity measuring device 50A further comprising a system of photodiodes 72 is presented for detecting and measuring height level changes in vertical tube 53. Each photodiode 72 comprises a first connection wire 73 and a second connection wire 74. Second connection wire 74 is connected to a power source (e.g., a 5V DC power source), and first connection wire 73 delivers an output signal. First connection wire 73 connects to resistor 75, which in turn connects to ground 76. Photodiode 72 is activated by light source 71. In order to assist the transmission of light from light source 71 to photodiode 72, a plurality of light-guide channels 78, each having a cylindrical shape is provided. Each photodiode 72 is inserted into one end of each light-guide channel 78 such that only light source 71 may enter a light-guide channel 78 to activate a photodiode 72.

Figure 4:
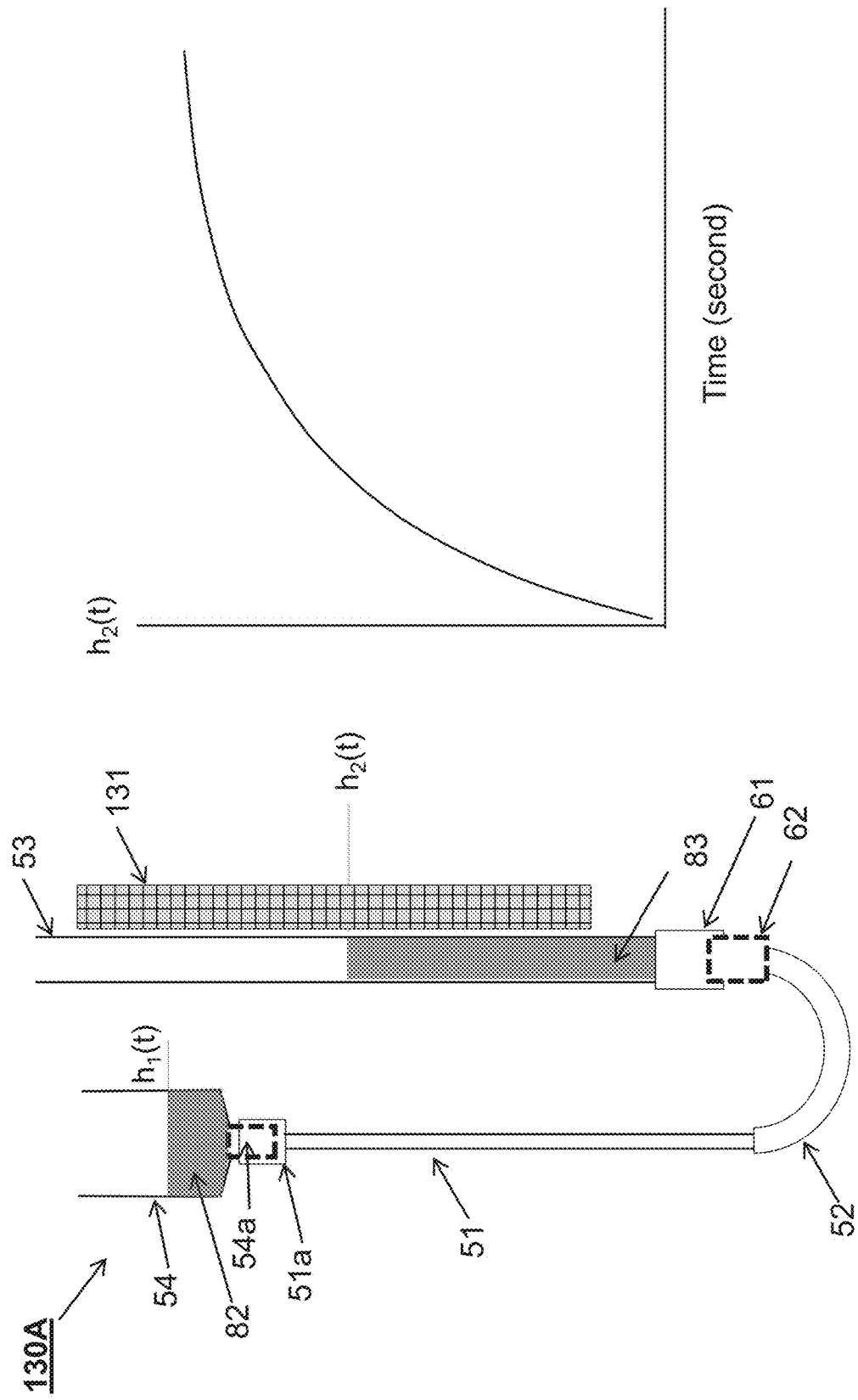
FIG. 4 depicts a diagram of a contact image sensor for transient liquid level measurements in the vertical tube of an exemplary viscosity measuring device of the present invention.

Referring now to FIG. 4, an exemplary viscosity measuring device 130A further comprising a contact image sensor 131 is depicted. Contact image sensor 131 measures liquid height changes in vertical tube 53. Contact image sensor 131 comprises LEDs and photodiodes, as would be understood by those skilled in the art, to measure height changes in vertical tube 53 over time. The change in liquid height over time is described as $h_2(t)$.

Figure 5:
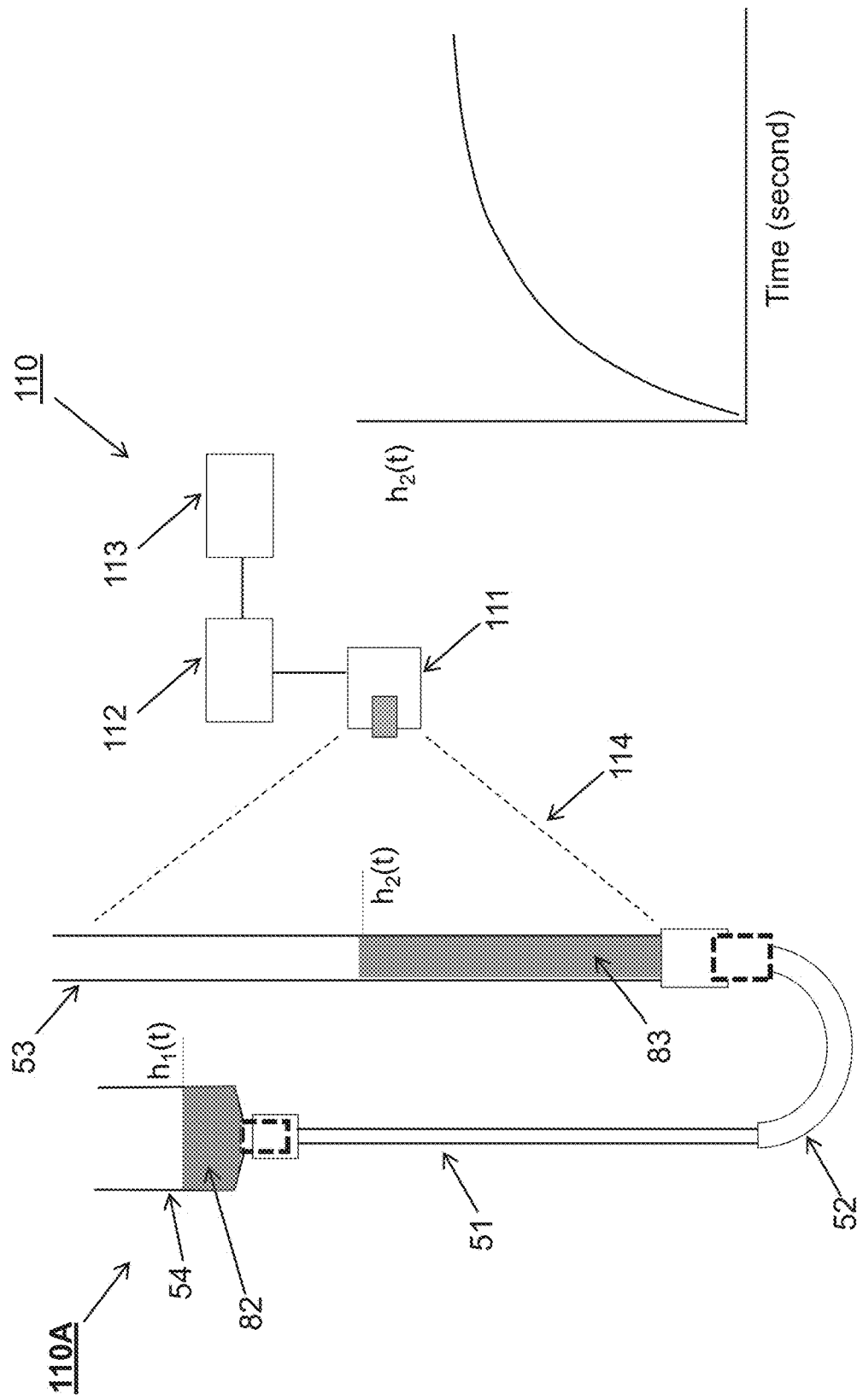
FIG. 5 depicts a diagram of a CCD video camera system for transient liquid level measurements in the vertical tube of an exemplary viscosity measuring device of the present invention.

Referring now to FIG. 5, an exemplary viscosity measuring device further comprising a CCD video camera system 110 is depicted. CCD video camera system 110 comprises CCD video camera 111, software program 112, and microprocessor 113. CCD video camera 111 comprises view window 114 providing coverage of the entire height of vertical tube 53. Camera 111 detects and records changes in liquid level in vertical tube 53. Software program 112 detects, analyzes, and converts changes in liquid level $h_2(t)$ in the form of data and inputs the data into microprocessor 113. Software program 112 may be any suitable software program capable of tracking and measuring movement, such as a program that utilizes an edge detection method (J. Canny, "A computational approach to edge detection," Pattern Analysis and Machine Intelligence, IEEE Transactions on, pp. 679-698, 1986: E. Nadernejad, S. Sharifzadeh, and H. Hassanpour, "Edge detection techniques: evaluations and comparison," Applied Mathematical Sciences, vol. 2, pp. 1507-1520, 2008; N. R. Pal and S. K. Pal, "A review on image segmentation techniques," Pattern recognition, vol. 26, pp. 1277-1294, 1993). The exemplary embodiment illustrated in FIG. 4 is able to measure height changes of opaque, semi-transparent, and transparent liquids by tracking the change in liquid height measured from the liquid meniscus.

Figure 6:
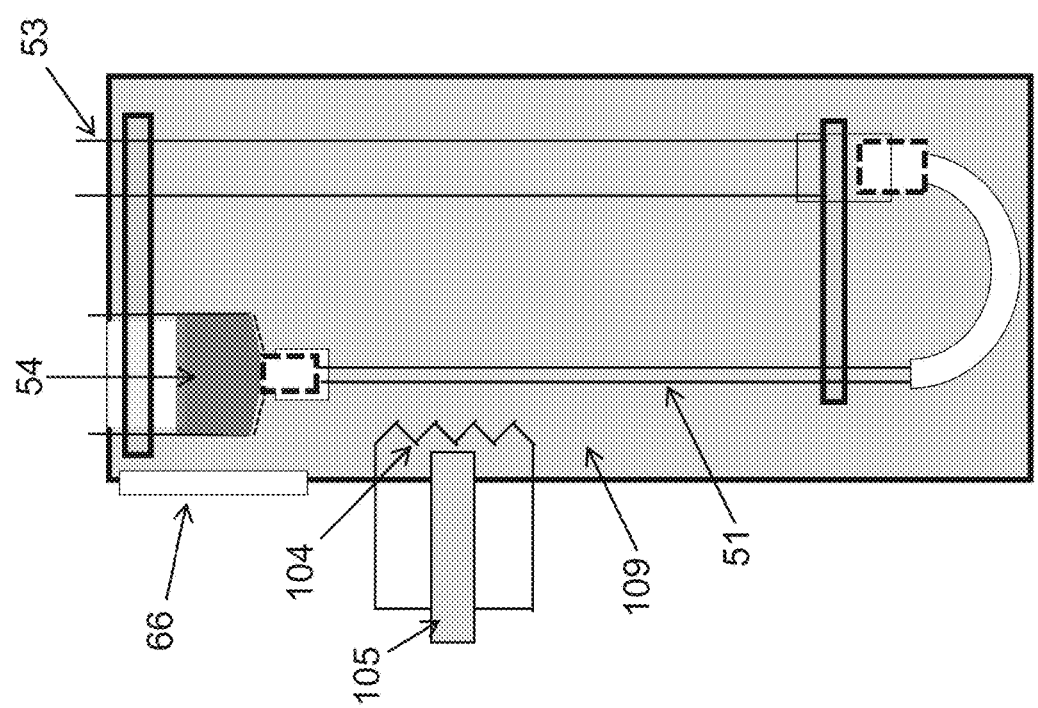
FIG. 6 depicts a diagram of a constant-temperature chamber for maintaining a constant prescribed temperature of both a liquid sample and an exemplary embodiment of the present invention.

Referring now to FIG. 6, an exemplary viscosity measuring device further comprising a temperature chamber 109 is depicted. Temperature chamber 109 is provided for measuring the viscosity of a liquid sample at a constant predetermined temperature. The temperature may be any temperature, such as an exemplary core body temperature of 37° C., a reduced body temperature of 25° C. (mimicking a patient undergoing cardiopulmonary bypass surgery), an elevated temperature of 100° C. (such as in fluid-related industrial drilling applications), and the like. As depicted in FIG. 5, U-shaped tube 50, linear light source 71, and the at least one photodiodes 72 are inside temperature chamber 109 during a viscosity test. Heater 104 is provided with a thermostat to deliver thermal energy to heat the air within temperature chamber 109 to a desired temperature. Fan 105 circulates the air to ensure the temperature within temperature chamber 109 is constant and uniform. While many viscosity tests may be performed at the core body temperature of 37° C., in the case where viscosity tests need to be performed at an ambient temperature such as 25° C., heater 104 is adjustable to provide a lower temperature in temperature chamber 109. In other embodiments, temperature chamber 109 may be provided with a feature for lowering the temperature below ambient temperature, such as a liquid bath or a heat pump (not pictured). Temperature chamber 109 comprises at least one transparent window 66 for the observation of liquid movement within the viscosity measuring device. In one embodiment, the liquid level $h_1(\infty)$ in reservoir 54, visible through transparent window 66, is measured at the conclusion of a viscosity test to determine surface tension of the liquid sample in calculation steps detailed below.

Viscosity Measuring Methods

Figure 7:
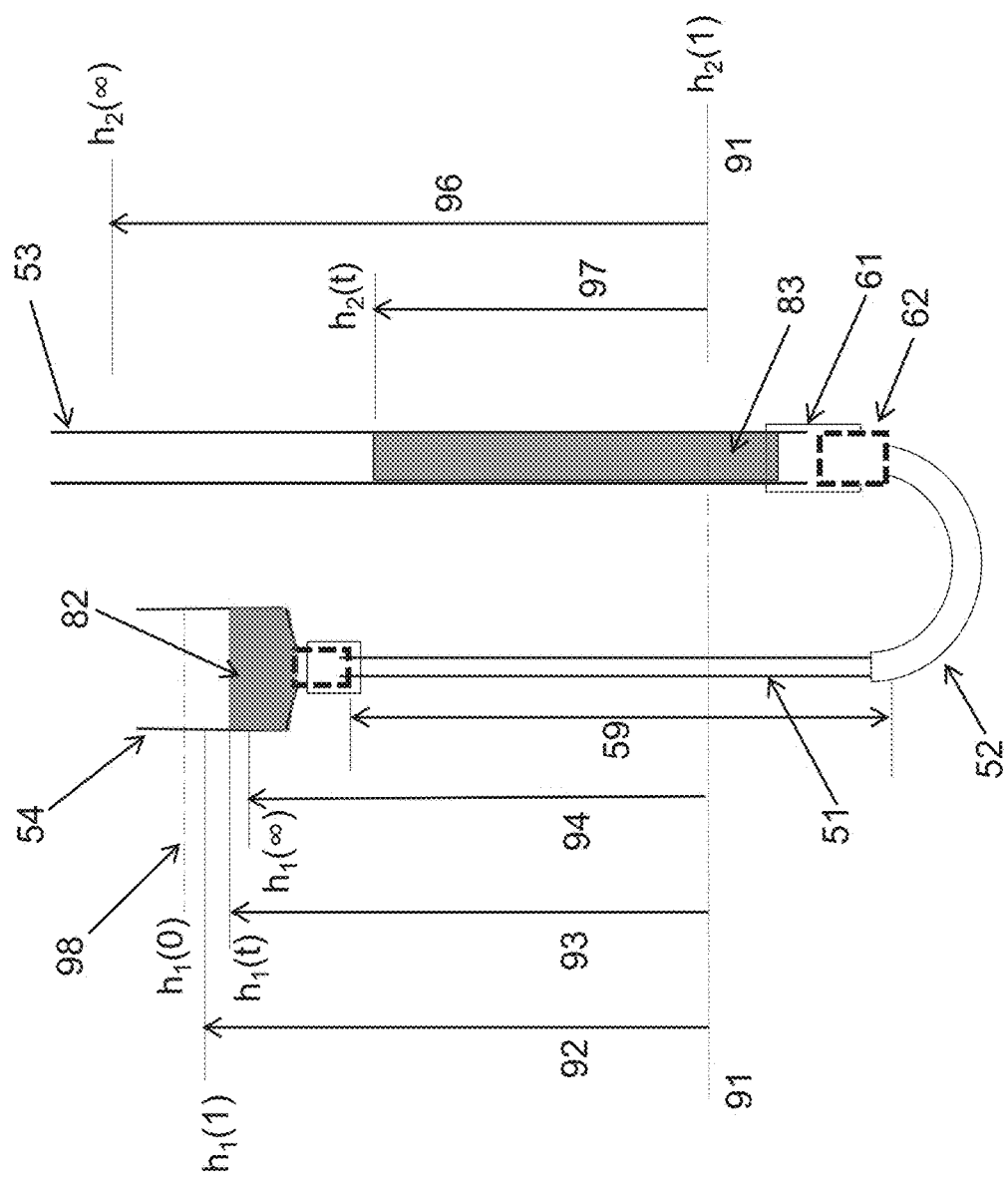
FIG. 7 depicts a diagram of an exemplary viscosity measuring device with relevant distance dimensions used in the mathematical analysis of the present invention.

Referring now to FIG. 7, an exemplary viscosity measuring device is depicted with relevant distance dimensions for use in a mathematical analysis to compute viscosity. The distance dimensions are described in the context of a photodiode-based viscosity measuring device. It should be understood that the distance dimensions may be adapted to fit the dimensions of any of the viscosity measuring devices of the present invention. Liquid levels are measured relative to horizontal reference line 91. The distance dimensions are as follows:

- 59—length of capillary tube 51
- 91—reference level; coincides with $h_2(1)$, height of a first photodiode
- 92—liquid level $h_1(1)$ in liquid reservoir 54 corresponding to when the liquid sample arrives at the first photodiode $h_2(1)$
- 93—liquid level $h_1(t)$ in liquid reservoir 54 at time t
- 94—liquid level $h_1(\infty)$ in liquid reservoir 54 at the end of a viscosity test
- 96—liquid level $h_2(\infty)$ in vertical tube 53 at the end of a viscosity test
- 97—liquid level $h_2(t)$ in vertical tube 53 at time t
- 98—liquid level $h_1(0)$ in liquid reservoir 54 at the beginning of a viscosity test As described below, the methods of the present invention incorporate calculations for wall shear stress $\tau_{wall}$ and wall shear rate $\dot{\gamma}_{wall}$ in capillary tube 51.

Determination of Wall Shear Stress

Wall shear stress in capillary tube 51 is determined from the force balance between the pressure drop across capillary tube 51 ($\Delta P_c$) and wall shear stress is given by the following equation:

$$\tau_{wall} = \frac{\Delta P_c \cdot d}{4L} \qquad \text{Eq. (2)}$$

where d is the diameter of capillary tube 51 and L is the length of capillary tube 51. The pressure drop $\Delta P_c$ across capillary tube 51 is given by the following equation:

$$\Delta P_c = P_{c1} - P_{c2} = \rho g[h_1(t) - h_2(t) + \Delta h_{st}] \qquad \text{Eq. (3)}$$

where $\rho$ is the density of the liquid sample, g is the gravity constant (9.8 m/s$^2$), and $\Delta h_{st}$ is the effect of the surface tension of liquid on the pressure drop $\Delta P_c$ across capillary tube 51. Applying Equation 3 to Equation 2 provides wall shear stress as the following equation:

$$\tau_{wall}(t) = \frac{\Delta P_c \cdot d}{4L} = \frac{d}{4L}\rho g[h_1(t) - h_2(t) + \Delta h_{st}] \qquad \text{Eq. (4)}$$

Therefore, when the height change at vertical tube 53, $h_2(t)$, is experimentally measured with respect to time during a viscosity test, the wall shear stress can be calculated using Equation 4. While $h_2(t)$ is experimentally measured using any of the detection methods described elsewhere herein, $h_1(t)$ can be mathematically determined using the following equation:

$$h_1(t) = h_1(1) - \left[\frac{D}{D_{resevoir}}\right]^2 \cdot [h_2(t) - h_2(1)] \qquad \text{Eq. (5)}$$

where $h_2(1)$ is the predetermined position of a first photodiode, $h_2(t)$ is the liquid height in vertical tube 53 at time t, D is the inner diameter of vertical tube 53, and $D_{resevoir}$ is the inner diameter of liquid reservoir 54. $h_1(1)$ is the liquid level in liquid reservoir 54 when the liquid sample reaches the first photodiode at $h_2(1)$; $h_1(1)$ is provided by the following equation:

$$h_1(1) = h_1(\infty) + \left[\frac{D}{D_{resevoir}}\right]^2 \cdot [h_2(\infty) - h_2(1)] \qquad \text{Eq. (6)}$$

where $h_1(\infty)$ is the liquid level in liquid reservoir 54 at the end of the viscosity test, a value that is measured experimentally at the end of the viscosity test.

Both $h_1(\infty)$ and $h_2(\infty)$ are affected by the surface tension of the liquid sample. In the present invention, surface tension $\sigma$ of the liquid sample can be experimentally determined as a function of the difference between $h_1(\infty)$ and $h_2(\infty)$ in the following equation:

$$\sigma = [h_2(\infty) - h_1(\infty)] \cdot \left[\frac{\rho g}{4}\right] / \left[\frac{1}{D} - \frac{1}{D_{resevoir}}\right] \qquad \text{Eq. (7)}$$

where $[h_2(\infty)-h_1(\infty)]$ represents the net capillary rise between liquid reservoir 54 and vertical tube 53. Referring back to Equation 4, the term $\Delta h_{St}$, representing the net capillary rise in the unit of liquid height change, can be expressed as:

$$\Delta h_{st} = [h_2(\infty) - h_1(\infty)] = \frac{4\sigma}{\rho g}\left[\frac{1}{D} - \frac{1}{D_{resevoir}}\right] \quad \text{Eq. (8)}$$

Determination of Newtonian Viscosity

The viscosity of a Newtonian liquid sample can be determined using the following mathematical procedure. Referring back to Equation 2, the pressure drop across capillary tube 51 can be described as:

$$\Delta P_c = \left[\frac{32\,\mu L}{d^2}\right] V_c \quad \text{Eq. (9)}$$

where $V_c$ is the mean flow velocity in capillary tube 51 having a diameter d and a length L. Using the law of conservation of mass flow rate, $V_c$ can be represented as:

$$V_c = V_R \cdot \left[\frac{D}{d}\right]^2 \quad \text{Eq. (10)}$$

where $V_R$ is flow velocity in vertical tube 53. $V_R$ can be represented as the first derivative of liquid height in vertical tube 53:

$$V_R = \frac{dh_2(t)}{dt} \quad \text{Eq. (11)}$$

combining Equation 10 with Equation 11, $V_c$ in capillary tube 51 can be represented in terms of mean flow velocity $V_D$ in vertical tube 53 as:

$$V_c = V_R \cdot \left(\frac{D}{d}\right)^2 = \left[\frac{dh_2(t)}{dt}\right] \cdot \left(\frac{D}{d}\right)^2 \quad \text{Eq. (12)}$$

Referring back to Equation 3, the pressure drop across capillary tube 51 can be expressed as:

$$\Delta P_c = \left[\frac{32\,\mu L}{d^2}\right] V_c = \rho g [h_1(t) - h_2(t) + \Delta h_{st.}] \quad \text{Eq. (13)}$$

Using the expression for $V_c$ in Equation 12, the viscosity of liquid $\mu$ can then be determined by the following equation:

$$\mu = \left[\frac{d^2}{32L}\right]\frac{\Delta P_c}{V_c} \quad \text{Eq. (14)}$$

As an example, consider viscosity measurement of a liquid using a capillary tube with inside diameter of 0.8 mm and length of 100 mm. When the height difference $h_1(t)-h_2(t)$ is 50 mm, the pressure drop $\Delta Pc$ is determined to be 490 Pa. The velocity of liquid sample flowing through the capillary tube is 0.025 m/s, which is determined from the first derivative of $h_2(t)$. Thus, using the equation in Equation (14), the viscosity of the liquid could be determined as 0.0039 Pa·s, or 3.9 mPa·s.

Determination of Wall Shear Rate and Non-Newtonian Viscosity

The procedure to determine the wall shear rate is now described. In a steady state laminar flow in a tube having a circular cross-section, the walls hear rate for a Newtonian fluid is given as:

$$\dot{\gamma}_{Newtonian} = \frac{8V_c}{d} \quad \text{Eq. (15)}$$

Substituting Equation 12 into Equation 15, the wall shear rate for a Newtonian fluid can be expressed as:

$$\dot{\gamma}_{Newtonian} = \frac{8}{d} \cdot \left[\frac{dh_2(t)}{dt}\right] \cdot \left[\frac{D}{d}\right]^2 \quad \text{Eq. (16)}$$

In one embodiment of the present invention, the power-law model is used to relate the wall shear stress to wall shear rate for non-Newtonian fluids, given by:

$$\tau_{wall} = k \cdot [\dot{\gamma}_{Newtonian}] \quad \text{Eq. (17)}$$

where k and n are two model constants in the power-law model (S. Middleman, Flow of high polymers; continuum and molecular rheology. New York, N.Y.: John Wiley & Sons, Inc., 1968). Note that once a set of data of the wall shear stress $\tau_{wall}$ and Newtonian shear rate $\dot{\gamma}_{Newtonian}$ are obtained from Equations (4) and (15), respectively, one can plot a curve of $\log(\tau_{wall})$ and $\log(\dot{\gamma}_{Newtonian})$. The power law index n, which is the slope of the curve, can be determined.

Once the power-law index n is determined the wall shear rate for non-Newtonian fluid $\dot{\gamma}_{NN}$ can be expressed as:

$$\dot{\gamma}_{NN} = \left[\frac{3n+1}{4n}\right] \cdot \frac{8V_c}{d} \quad \text{Eq. (18)}$$

In other words, the non-Newtonian shear rate $\dot{\gamma}_{NN}$ could be determined by multiplying a constant $[(3n+1)/4n]$ to the Newtonian shear rate $$\frac{8V_c}{d}.$$

Pump-Based Viscosity Measuring Device

Figure 8:
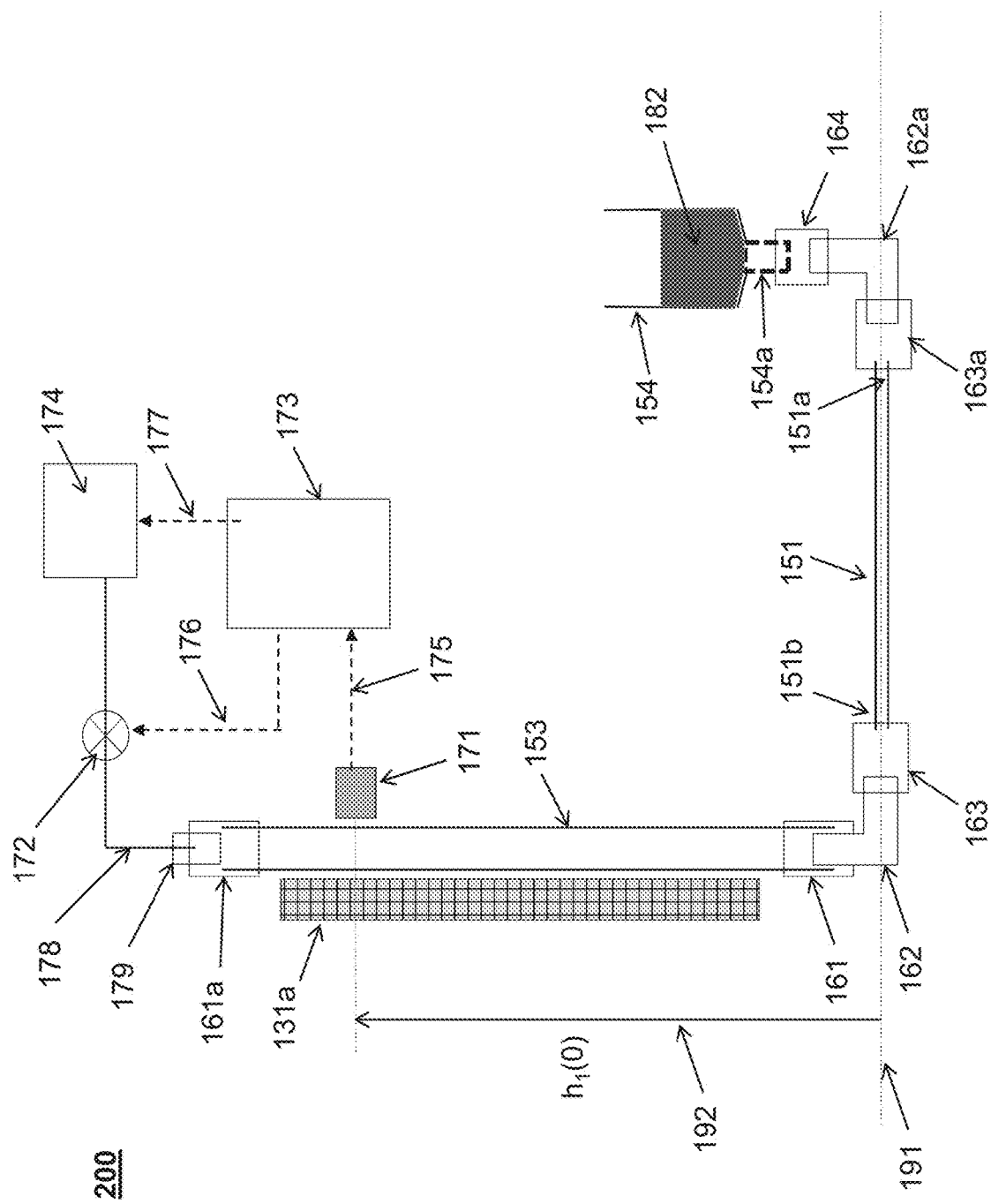
FIG. 8 depicts a diagram of an alternative exemplary viscosity measuring device of the present invention with a liquid reservoir at a lower level than the vertical tube, wherein a vacuum is used to introduce samples to the vertical tube.

Referring now to FIG. 8, an alternative exemplary viscosity measuring device 200 is depicted. Viscosity measuring device 200 comprises capillary tube 151, liquid reservoir 154, vertical tube 153, LED-CCD array 131a, vacuum pump 174, solenoid valve 172, sensor 171, and microprocessor 173. Liquid reservoir 154 can have any suitable dimensions. For example, liquid reservoir 154 can have a diameter between and 15 mm. Liquid reservoir 154 is positioned above capillary tube 151. Capillary tube 151 is aligned along horizontal reference line 191 and is connected to liquid reservoir 154 at its first end 151a by luer connection 164, elbow tube 162a, and luer connection 163a. Vertical tube 153 can have any suitable dimensions. For example, vertical tube 153 can have an inner diameter between 1 and 5 mm.

Vertical tube 153 is connected to a second end 151b of capillary tube 151 by luer connection 161, elbow tube 162, and luer connection 163. In some embodiments, liquid reservoir 154 is positioned at a height lower than vertical tube 153. In certain embodiments, the inside diameter of the capillary tube 151 is in the range of 0.4-1.0 mm, while the length of the capillary tube 151 is in the range of 50-100 mm. In certain embodiments, the inside diameter of the transparent vertical tube 153 is in the range of 2-3 mm, and the length of the vertical tube 153 is in the range of 50-120 mm. In certain embodiments, the size of the liquid reservoir 54 is in the range of 1-3 ml as the actual liquid sample volume 182 for viscosity test will be in the range of 1.5 ml.

Figure 9:
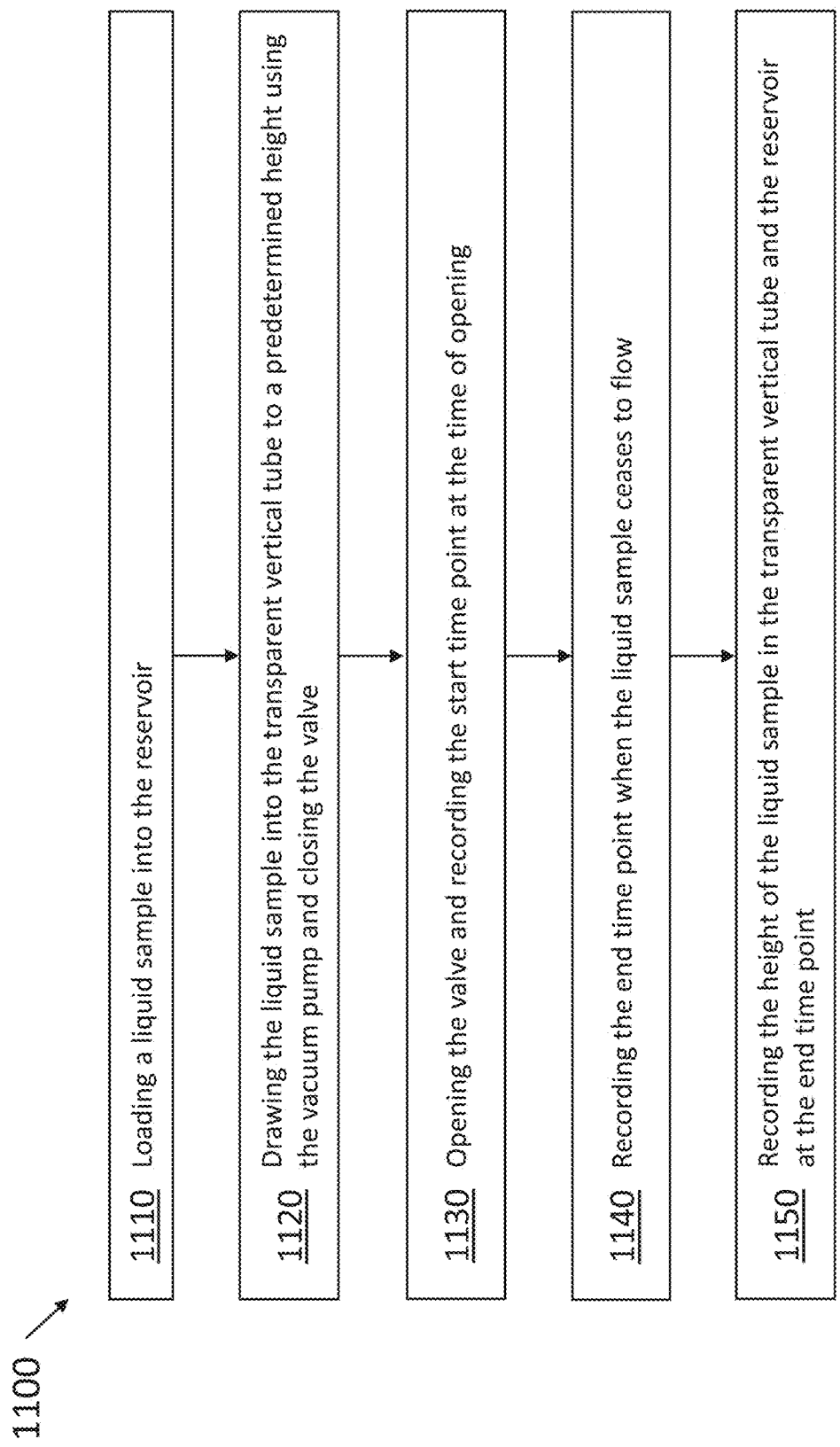
FIG. 9 is a flowchart depicting an exemplary method of using the viscosity measuring device of FIG. 8.

Referring now to FIG. 9, an exemplary method 1100 of using viscosity measuring device 200 is depicted. In step 1110, prior to the initiation of a viscosity test, a predetermined amount of a liquid sample 182 (e.g. 1 mL) is introduced to liquid reservoir 154. A predetermined amount of a liquid sample enables accurate measurement of liquid heights. For example, with a predetermined amount of a liquid sample, a specific liquid height in vertical tube 153 will correspond to a specific liquid height in liquid reservoir 154. Therefore, a predetermined amount of a liquid sample enables the determination of the liquid height in liquid reservoir 154 based on measuring only the liquid height in vertical tube 153. In some embodiments, a calibration curve is generated to correlate liquid height in vertical tube 153 with liquid height in liquid reservoir 154 using a predetermined amount of liquid sample prior to a viscosity test.

Figure 10:
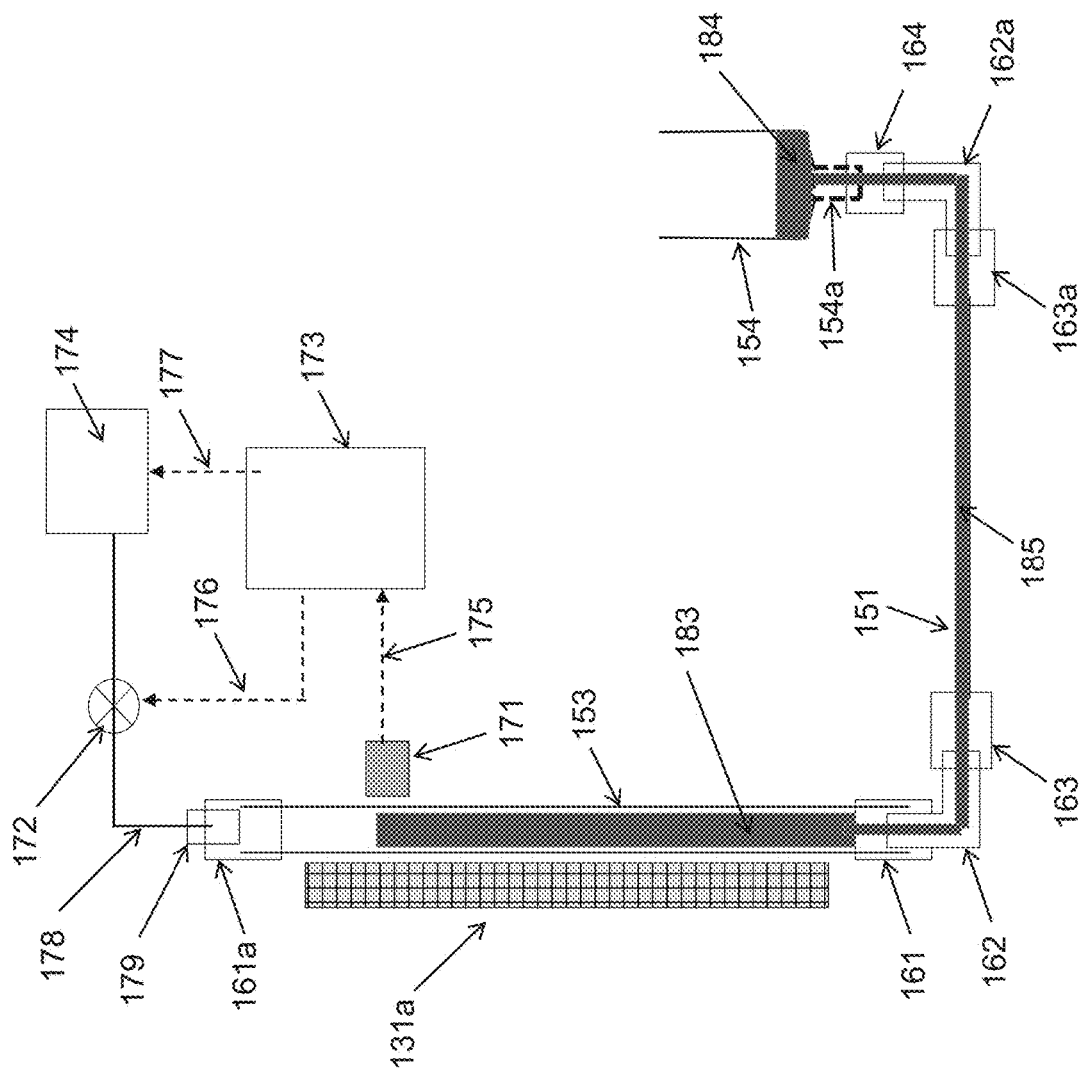
FIG. 10 depicts a diagram of an alternative exemplary viscosity measuring device of the present invention with a vacuum pump moving a liquid sample to a desired position in the vertical tube.

In step 1120, liquid sample 182 is drawn to vertical tube 153 by vacuum pump 174 at the top of vertical tube 153 after opening solenoid valve 172. As liquid sample 182 is drawn into vertical tube 153, the level of liquid sample 182 rises to a predetermined height indicated as $h_1(0)$ 192 in FIG. 8. Sensor 171, positioned at predetermined height $h_1(0)$ 192, detects the arrival of liquid sample 182 and sends a signal 175 to microprocessor 173 (FIG. 10). In response, microprocessor 173 sends a signal 176 to solenoid valve 172 causing it to close and stop the movement of liquid sample 182 within vertical tube 153. Microprocessor 173 also sends a signal 177 to vacuum pump 174 to turn off pump 174. Viscosity measuring device 200 is now prepared to initiate a viscosity test.

Figure 11:
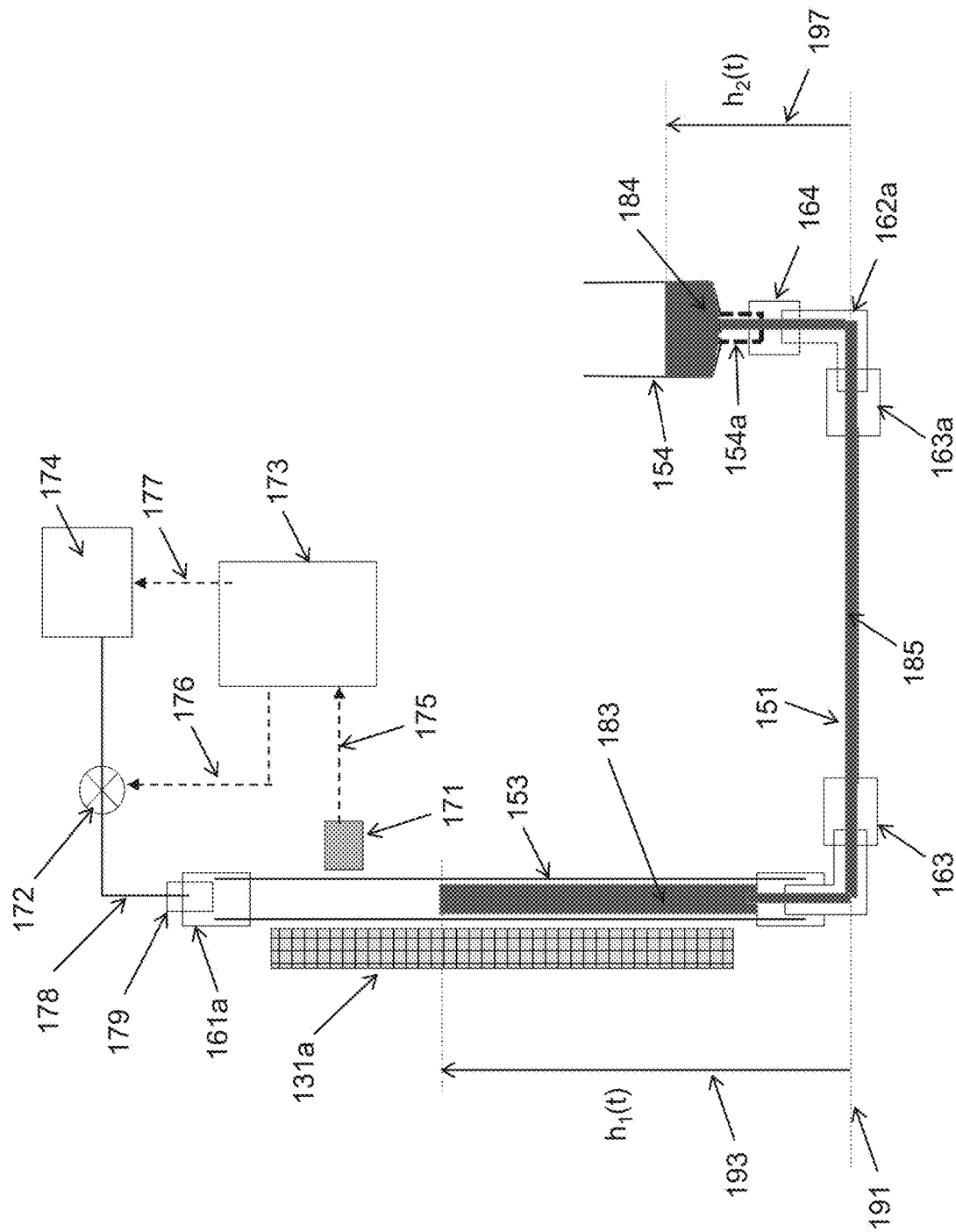
FIG. 11 depicts a diagram of an alternative exemplary viscosity measuring device of the present invention showing the liquid sample level in the vertical tube during a test.

In step 1130, the viscosity test is initiated at a recorded starting time point by microprocessor 173 sending a signal 176 to solenoid valve 172 causing it to open, allowing liquid sample in 183 to fall inside vertical tube 153 by gravity and flow through capillary tube 151 (FIG. 11). The height of liquid sample 183 in vertical tube 153, indicated by $h_1(t)$ 193, gradually decreases over time and approaches the height of liquid sample 184 in liquid reservoir 154, indicated by $h_2(t)$ 197.

Figure 12:
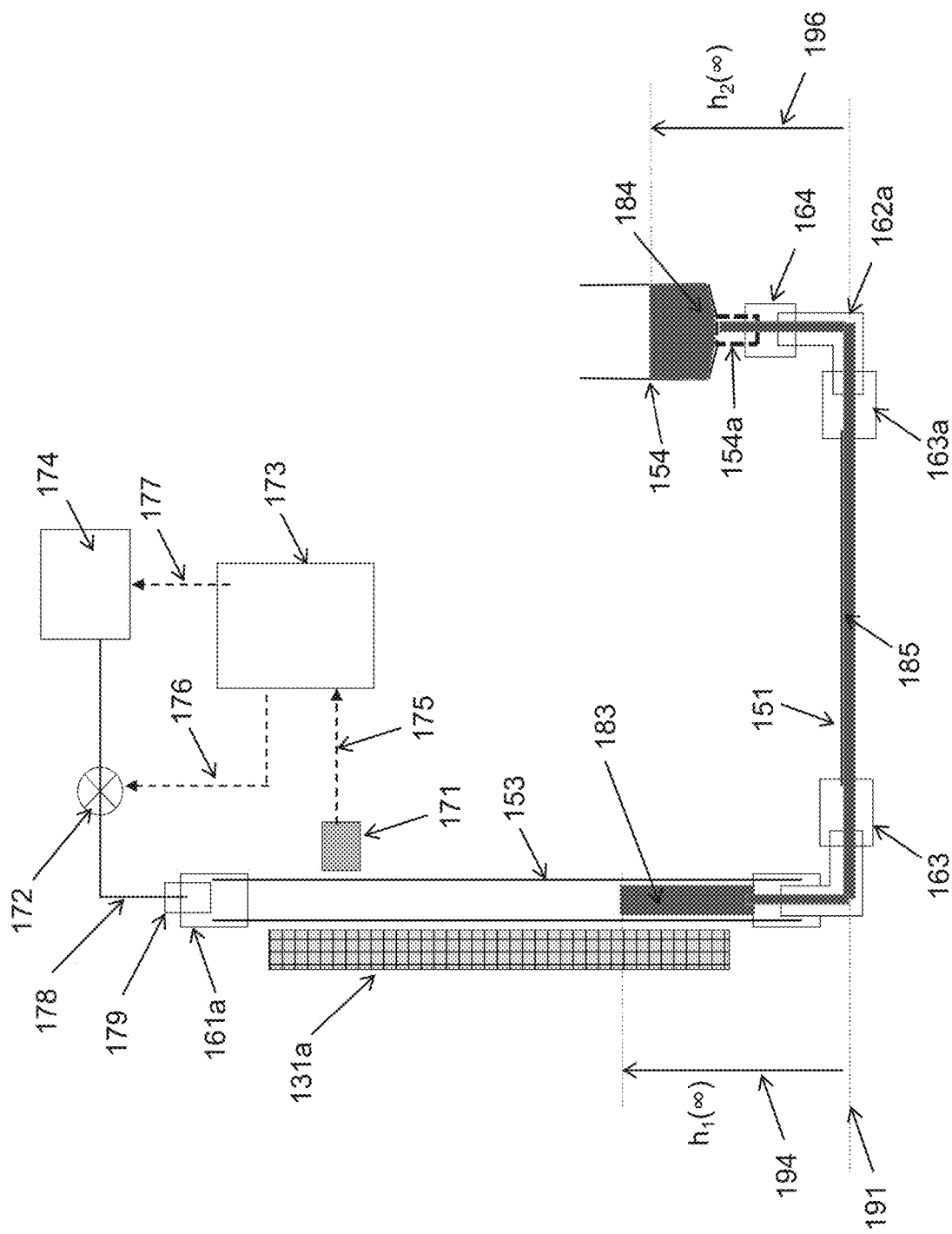
FIG. 12 depicts a diagram of an alternative exemplary viscosity measuring device of the present invention showing the liquid sample level in the vertical tube at the end of a test.

The change in height slows over time and eventually stops flowing (FIG. 12). In step 1140, the end time point when the liquid sample stops flowing is recorded. In step 1150, the heights of the liquid sample in vertical tube 153 and liquid reservoir 154 are recorded. The magnitude of surface tension in vertical tube 153 is much greater than in liquid reservoir 154, as surface tension is inversely proportional to the inside diameter of a vessel. As a result, at the conclusion of a viscosity test in FIG. 12, the liquid level $h_1(\infty)$ 194 in vertical tube 153 is higher than the liquid level $h_2(\infty)$ 196 in liquid reservoir 154.

Pump-Based Viscosity Measuring Methods

The method of calculating viscosity using viscosity measuring device 200 is now described. As liquid height $h_1(t)$ 193 decreases in vertical tube 153, the height change is detected by any of the aforementioned means, for example by LED-CCD array 131a depicted in FIG. 11. As previously described herein, pressure drop $\Delta P_c$ across capillary tube 185 is represented by:

$$\Delta P_c = P_{c1} - P_{c2} = \rho g[h_1(t) - h_2(t) + \Delta h_{st}] \qquad \text{Eq. (3)}$$

where ρ is the density of liquid sample 184 and g is the gravity constant (i.e., 9.8 m/s²).

As previously described herein, the height change $\Delta h_{st}$ due to the surface tension difference between vertical tube 153 and liquid reservoir 154 in viscosity measuring device 200 is represented by:

$$\Delta h_{st} = [h_2(\infty) - h_1(\infty)] = \frac{4\sigma}{\rho g}\left[\frac{1}{D} - \frac{1}{D_{reservoir}}\right] \qquad \text{Eq. (8)}$$

where $h_1(\infty)$ 194 is the liquid height in vertical tube 153 at the end of the viscosity test and $h_2(\infty)$ 196 is the liquid height in liquid reservoir 154 at the end of the viscosity test (FIG. 12). Applying the pressure drop expression across capillary tube 151, the formula for wall shear stress can be expressed as previously described herein:

$$\tau_{wall}(t) = \frac{\Delta P_c \cdot d}{4L} \frac{d}{4L} \rho g[h_1(t) - h_2(t) + \Delta h_{st}] \qquad \text{Eq. (4)}$$

The derivative of height $h_1(t)$ 193 in vertical tube 153 becomes $dh_1/dt$, which is the flow velocity $V_R$ at vertical tube 153. Diameter D of vertical tube 153 and diameter d of capillary tube 151 are predetermined; the formula for flow velocity $V_c$ at capillary tube 151 can be expressed as previously described herein:

$$V_c = V_R \cdot \left[\frac{D}{d}\right]^2 \qquad \text{Eq. (10)}$$

The procedures for determining liquid viscosity and shear rate are the same as the ones provided in Equations 15-18 elsewhere herein.

Pressure-Based Viscosity Measuring Device

Figure 13:
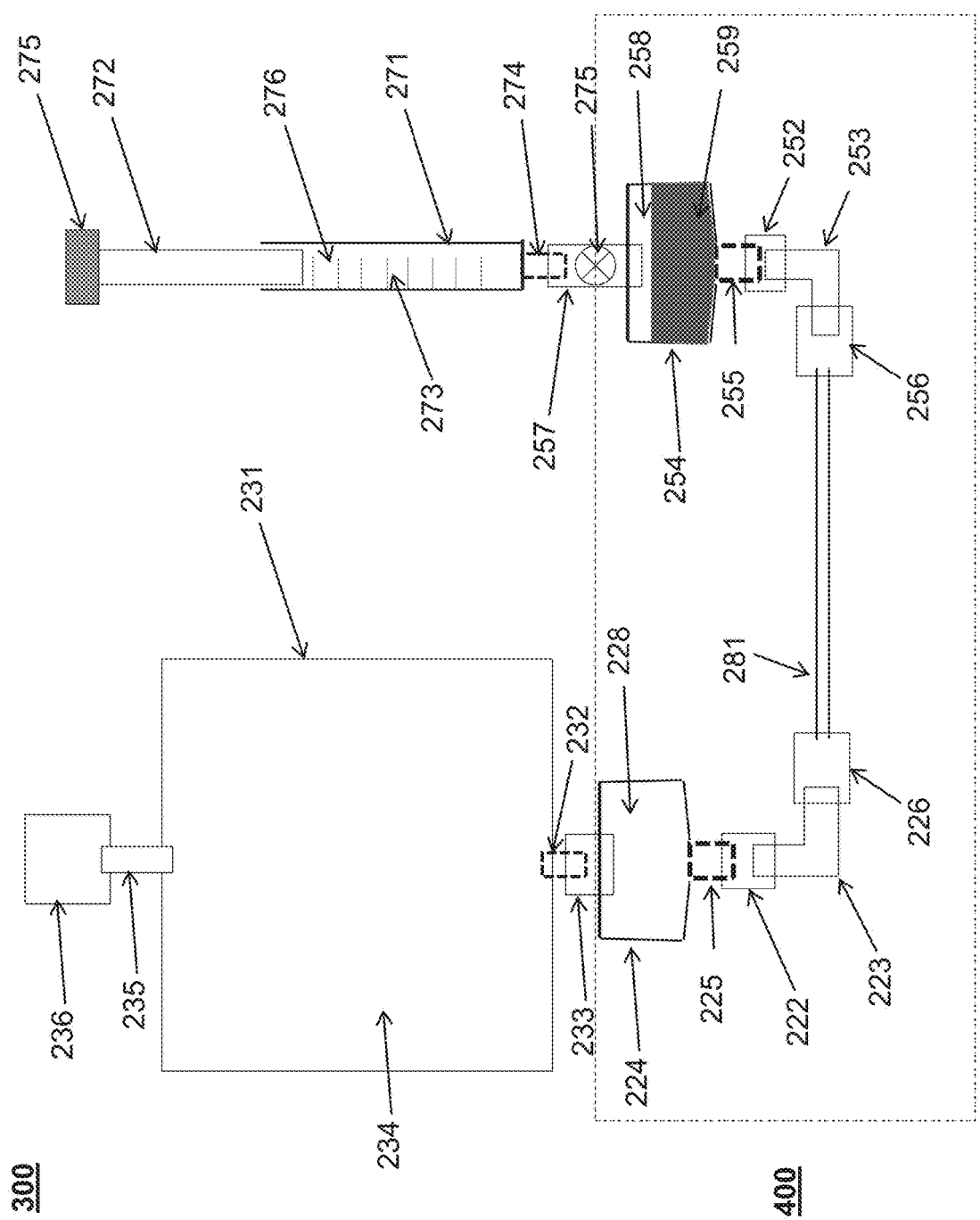
FIG. 13 depicts a diagram of an alternative exemplary viscosity measuring device of the present invention with a large air chamber, where compression force is used to introduce liquid samples to the upstream liquid reservoir at high pressure.

Referring now to FIG. 13, another alternative exemplary viscosity measuring device 300 is depicted. Viscosity measuring device 300 measures viscosity as a function of pressure change over time and comprises a first liquid reservoir 254, a second liquid reservoir 224, a capillary tube 281, a large air chamber 213 filled with air 234, a pressure transducer 236, and a syringe 271. First liquid reservoir 254 and second liquid reservoir 224 can have any suitable size. For example, first liquid reservoir 254 and second liquid reservoir 224 can have diameters between 1 and 2 cm. Air chamber 231 can have any suitable size. For example, air chamber 231 can be dimensioned to hold a volume of 10 to 100 mL. Syringe 271 can be any suitable syringe, comprising a plunger 276 and piston 272. In some embodiments, syringe 271 comprises a locking mechanism to at least partially lock piston 272. Syringe 271 is fluidly connected to first liquid reservoir 254 by luer connection 257 and valve 275. Valve 275 can be opened and closed to introduce ambient air to the fluid connection between syringe 271 and first liquid reservoir 254. In certain embodiments, the inside diameter of the capillary tube 281 is in the range of 0.4-1.0 mm, while the length of the capillary tube 281 is in the range of 50-100 mm. In certain embodiments, the size of the liquid reservoir 254 is in the range of 1-3 ml as the actual liquid sample volume 259 for viscosity test will be in the range of 1.5 ml.

First liquid reservoir 254 is fluidly connected to one end of capillary tube 281, for example by luer connection 252, elbow tube 253, and luer connection 256. In some embodiments, viscosity measuring device 300 comprises a flow-control mechanism as described elsewhere herein, such as a clamp attached to elbow tube 253 (not pictured). The opposite end of capillary tube 281 is fluidly connected to second liquid reservoir 224, for example by luer connection 226, elbow tube 223, and luer connection 222. Second liquid reservoir 224 is fluidly connected to air chamber 213, for example by luer connection 233. The fluid connection between syringe 271, first liquid reservoir 254, capillary tube 281, second liquid reservoir 224, and air chamber 213 is airtight, such that the fluid connection may be pressurized without loss of air or liquid. Air chamber 213 is fluidly connected to pressure transducer 236 by pipe 235, such that the pressure within air chamber 213 may be measured by pressure transducer 236. Pressure transducer 236 is preferably a high accuracy pressure transducer capable of measuring pressure variations in the range of 0 to 3000 Pa. For example, a pressure transducer from Omega Engineering (PX429-10WG5V) can be used.

In some embodiments, viscosity measuring device 300 may be modular, such that a plurality of components may be provided in a single module. For example, as depicted in FIG. 13, a dashed rectangular box indicates the components that are included in an exemplary module 400. Module 400 comprises at least second liquid reservoir 224, capillary tube 281, first liquid reservoir 254, and any suitable connections and tubes necessary to create a fluid connection between second liquid reservoir 224, capillary tube 281, and first liquid reservoir 254. Module 400 may also comprise the other components of a viscosity measuring device. Module 400 provides a means to quickly and conveniently exchange device components between viscosity tests. Viscosity measuring devices comprising modules increase ease of use and decrease the risk of contamination. In some embodiments, all of the relevant components may be packed into a small module, such as a module that is about the size of a credit card.

Figure 14:
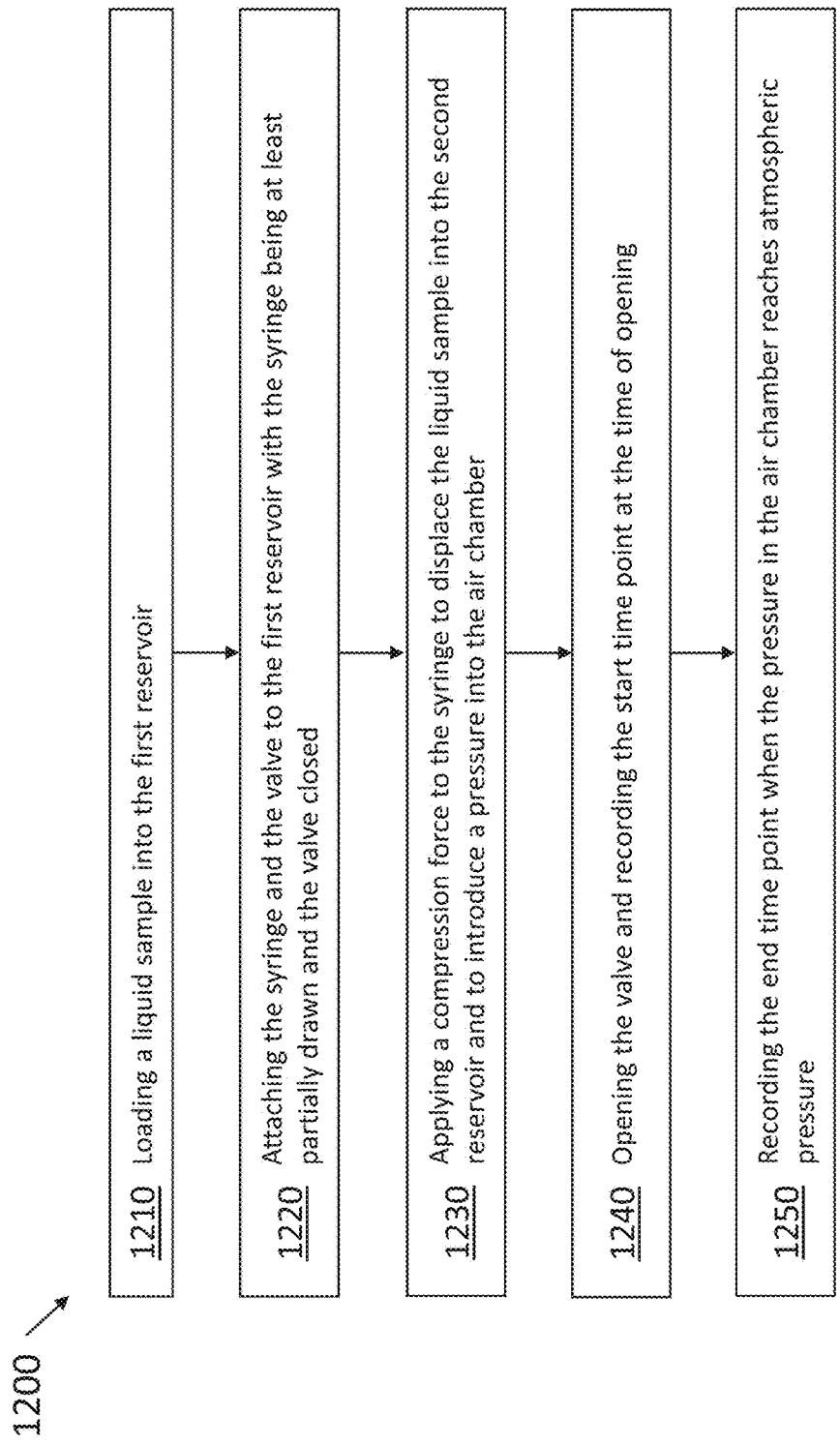
FIG. 14 is a flowchart depicting an exemplary method of using a viscosity measuring device of FIG. 13.
Figure 15:
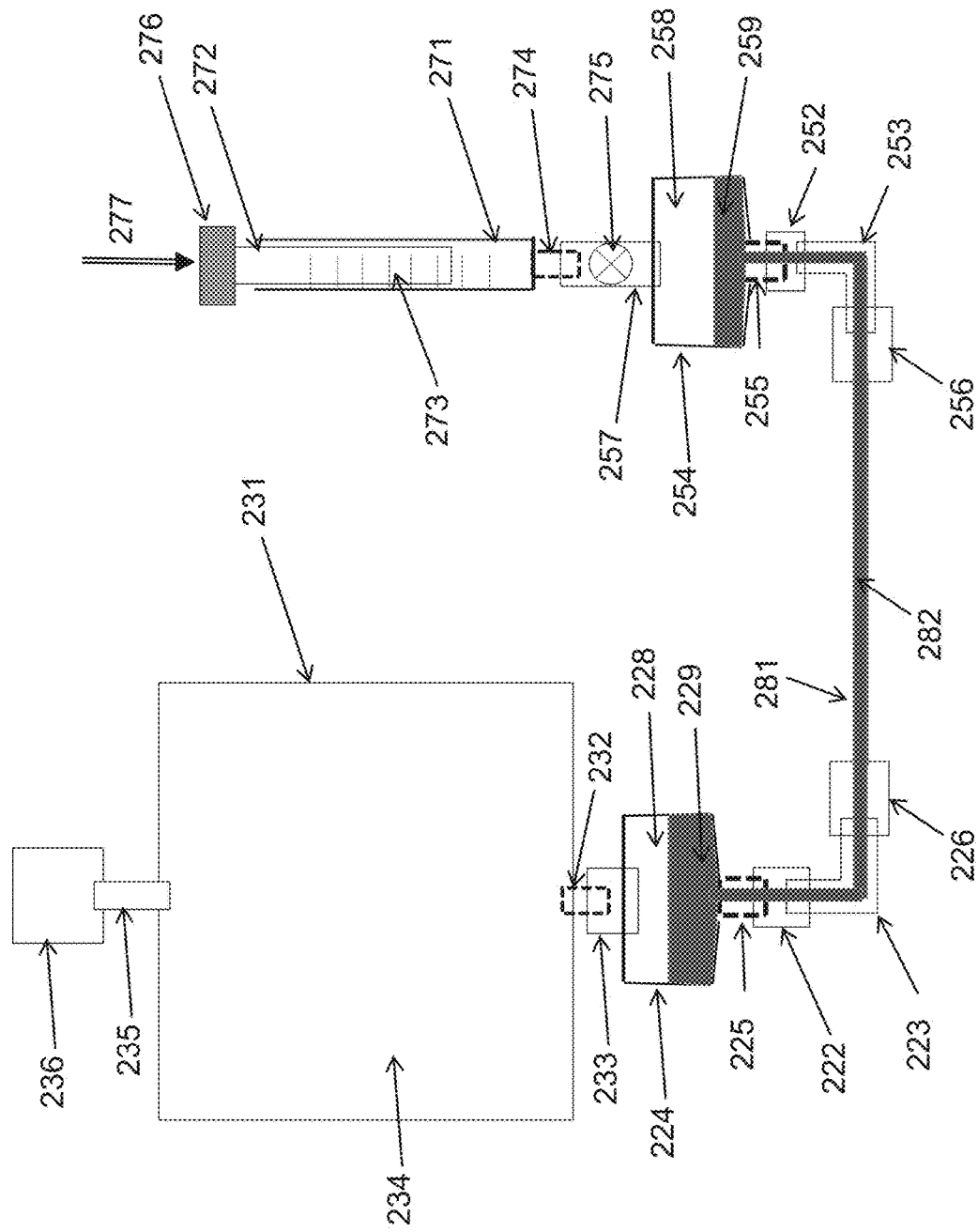
FIG. 15 depicts a diagram of an alternative exemplary viscosity measuring device of the present invention with a large air chamber, where a liquid sample is in the upstream liquid reservoir at high pressure.
Figure 16:
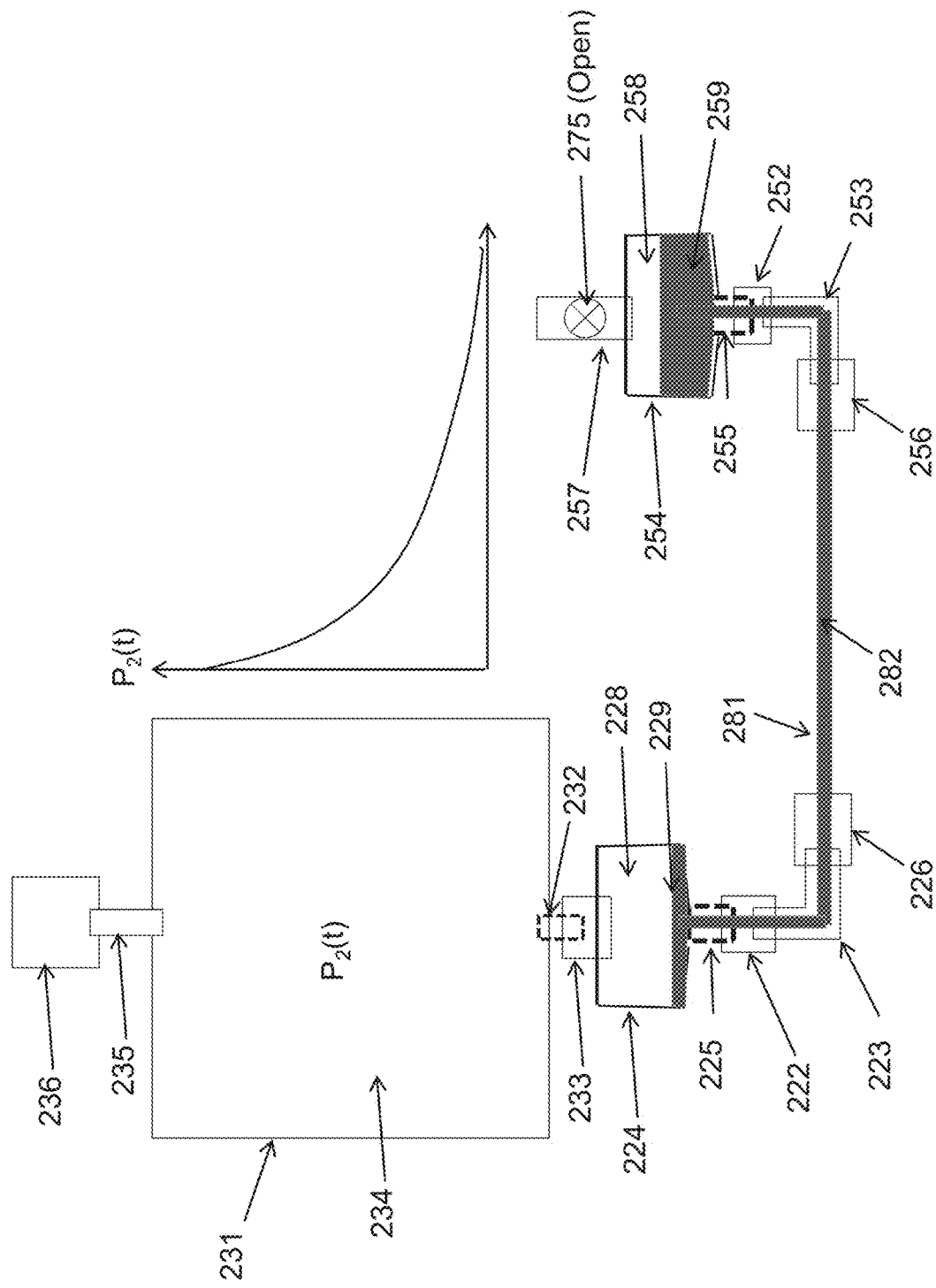
FIG. 16 depicts a diagram of an alternative exemplary viscosity measuring device of the present invention with a large air chamber, where the pressure has been relieved and the viscosity test has concluded.

Referring now to FIG. 14, an exemplary method 1200 of using viscosity measuring device 300 is depicted. In step 1210, prior to a viscosity test, liquid sample 259 is loaded into first liquid reservoir 254. In step 1220, syringe 271 and valve 275 are attached, wherein syringe 271 is at least partially drawn with plunger 272 and piston 272 at least partially extended and valve 275 closed. In step 1230, a compression force 277 is used upon syringe 271 to introduce liquid sample 259 from first liquid reservoir 254 to second liquid reservoir 224 connected to air chamber 231 (FIG. 15). This transport of liquid sample 259 decreases the total air volume 234 throughout viscosity measuring device 300, including air chamber 231, thereby increasing the pressure in air chamber 231 prior to the viscosity test (i.e., t<0).

In step 1240, the viscosity test is initiated at a recorded starting time point by opening valve 275, thereby relieving the pressure and allowing liquid sample 259 to flow from second liquid reservoir 224 back to first liquid reservoir 254. As liquid sample 259 flows back into first liquid reservoir 254, the pressure in air chamber 231 gradually decreases until it reaches atmospheric pressure, whereupon liquid sample 259 stops flowing. In step 1250, the end time point when the pressure in air chamber 231 returns to atmospheric pressure is recorded. The aforementioned steps of preparing and initiating a viscosity test using viscosity measuring device 300 may be repeated on a liquid sample to improve the accuracy of results.

Viscosity measuring device 300 uses pressure change over time to calculate the viscosity of a liquid sample. During a viscosity test, the pressure $P_2(t)$ in air chamber 231 and second liquid reservoir 224 decreases exponentially, as depicted in FIG. 15. Accordingly, flow velocity $V_c$ of liquid sample at capillary tube 281 is large just as the viscosity test is initiated but also decreases exponentially with time until flow velocity $V_c$ reaches zero at the end of the test. Further, wall shear rate at capillary tube 281 is also large just as the viscosity test is initiated but decreases exponentially with time until wall shear rate reaches zero at the end of the test. By measuring viscosity as a function of pressure change over time in air chamber 231, viscosity measuring device 300 is capable of accurately measuring viscosity over a wide shear rate range, such as between 1 and 1000 $s^{-1}$.

Viscosity measuring device 300 is able to measure the viscosity of very small volumes of liquid samples. For example, viscosity measuring device 300 is capable of accurately measuring volumes between 0.1 and 1 mL. Accordingly, air chamber 231 can have a suitably small volume as well. In some embodiments, air chamber 231 can have a volume between 10 and 100 mL. The volume of air chamber 231 affects the maximum pressure within air chamber 231 when the air is displaced by a loaded liquid sample. For example, when a liquid sample of 0.5 mL is loaded prior to a viscosity test, an air chamber 231 with a volume of 30 mL has a maximum pressure of 102,683 Pa (absolute); an air chamber 231 with a volume of 50 mL has a maximum pressure of 102,010 Pa (absolute); and an air chamber 231 with a volume of 70 mL has a maximum pressure of 101,721 Pa (absolute).

Pressure-Based Viscosity Measuring Methods

The method of calculating viscosity using viscosity measuring device 300 is described as follows. As described previously, pressure in air chamber 231 and second liquid reservoir 224 is described as $P_2(t)$. During a viscosity test, with valve 275 open, pressure in first liquid reservoir 254 is described as $P_1$, which is constant at atmospheric pressure (101,000 Pa). Pressure drop across capillary tube 281 is expressed as $\Delta P_c$. As previously described herein, the wall shear stress $\tau_{wall}$ on the surface of capillary tube 281 is represented by:

$$\tau_{wall} = \frac{\Delta P_c \cdot d}{4L} \qquad \text{Eq. (2)}$$

where d is the diameter and L is the length of capillary tube 281. Using pressure $P_2(t)$ at the air chamber 231 and second liquid reservoir 224 and pressure $P_1$ at first liquid reservoir 254, pressure drop $\Delta P_c$ across capillary tube 281 can be expressed as:

$$\Delta P_c = P_2(t) - P_1 - \Delta P_{th} \qquad \text{Eq. (19)}$$

where the $\Delta P_{th}$ is the pressure drop due to the liquid height difference between first liquid reservoir 254 and second liquid reservoir 224. While the effect of $\Delta P_{th}$ on pressure drop $\Delta P_c$ may be relatively small, the present invention measures $\Delta P_{th}$ to account for any difference in liquid sample height between first liquid reservoir 254 and second liquid reservoir 224.

Air volume change in air chamber 231 and the fluidly connected components downstream from liquid sample 259 is equal to the volume of liquid sample 259 displaced into capillary tube 281 during the preparation steps prior to the initiation of a viscosity test. Accordingly, volume flow rate and flow velocity $V_c$ at capillary tube 281 can be expressed as:

$$V_c = \frac{VOL_2(t)}{A_c}\left[\frac{\left(\frac{dP_2(t)}{dt}\right)}{P_2(t)}\right] \quad \text{Eq. (20)}$$

where $VOL_2(t)$ is the volume of air in air chamber 231 and the fluidly connected components downstream from liquid sample 259, and $A_c$ is the cross-sectional area of capillary tube 281. Wall shear rate $\dot{\gamma}_{wall}$ at capillary tube 281 can then be expressed as:

$$\dot{\gamma}_{wall} = \left(\frac{8}{d}\right)\frac{VOL_2(t)}{A_c}\left[\frac{\left(\frac{dP_2(t)}{dt}\right)}{P_2(t)}\right] \quad \text{Eq. (21)}$$

Using the wall shear stress and wall shear rate, viscosity μ of a liquid sample can be expressed as:

$$\mu = \left(\frac{A_c \cdot d^2}{32 \cdot L \cdot VOL_2(t)}\right)\left[\frac{(P_2(t) - P_1 - \Delta P_{th}) \cdot P_2(t)}{\left(\frac{dP_2(t)}{dt}\right)}\right] \quad \text{Eq. (22)}$$

Improvements Over Prior Art

A dual-riser (vertical tube) and single capillary viscometer technique described in the prior art utilizes an inlet and an outlet vertical tubes of the same diameter assembled in a U-shaped tube (K. Kensey and Y. Cho, "Method for determining the viscosity of an adulterated blood sample over plural shear rates," 2004; K. Kensey, W. N. Hogenauer, S. Kim, and Y. Cho, "Dual riser/single capillary viscometer," 2002; S. Kim, Y. Cho, W. Hogenauer, and K. Kensey, "A method of isolating surface tension and yield stress effects in a U-shaped scanning capillary-tube viscometer using a Casson model" Journal of Non-Newtonian Fluid Mechanics, vol. 103, pp. 205-219, 2002). The liquid sample to be measured falls through one inlet vertical tube and moves through a capillary tube into the second outlet vertical tube because of the height difference in the two vertical tubes. The differential pressure across the capillary tube ($P_{inlet}$-$P_{outlet}$) is always "positive" during the entire period of the test, meaning that $P_{inlet}$>$P_{outlet}$, as the liquid height in the inlet vertical tube is consistently greater than that in the outlet vertical tube. Furthermore, while the differential pressure across the capillary tube decreases with time it remains "positive" during the entire test period.

The present invention also uses a U-shaped tube but differs conceptually in numerous unique ways, for example the present invention employs only one outlet vertical tube in one leg of the U-shaped tube. In place of the inlet vertical tube used in the prior art, the U-shaped tube in the present invention incorporates a liquid reservoir for holding and introducing the liquid sample to be tested. The inside diameter of this reservoir is substantially greater (such as about four-fold or more) than that of the outlet vertical tube. In the present invention, the liquid moves through the capillary tube initially by gravity, with the assistance of a plunger and deadweight, or by a pumping mechanism.

However, as the liquid height in the vertical tube approaches the liquid level in the reservoir, the driving mechanism for the flow of liquid during the viscosity test is no longer gravity but the force of surface tension. More specifically, the differential pressure across the capillary tube ($P_{inlet}$-$P_{outlet}$) decreases with time during the beginning of a viscosity test. However, as the viscosity test progresses, the differential pressure across the capillary tube approaches zero, $P_{inlet}$=$P_{outlet}$, and then becomes "negative", meaning $P_{inlet}$<$P_{outlet}$, as the liquid height in the vertical tube is greater than the liquid height in the reservoir. In other words, the differential pressure across the capillary tube does not decrease with time during the beginning of a viscosity test in the present invention, but rather increases with time.

In spite of the fact that the differential pressure across the capillary tube of the present invention becomes "negative" as the viscosity test progresses, the liquid sample continues to move through the capillary tube because the surface tension of the liquid sample provides sufficient force to pull the liquid sample against the force of gravity. In other words, the present invention utilizes the surface tension force as the driving force to move the liquid sample through the capillary tube in a viscosity test, when the fluid shear rate values are the lowest. This is one of the fundamental differences of the present invention vis-á-vis the prior art: measuring liquid viscosity based on a fluid dynamic principle involving surface tension rather than gravity alone.

In another aspect, the capillary tube viscometer described in the prior art utilizing only gravity to drive two vertical tubes in a U-shape tube is inaccurate when measuring the viscosity of sticky liquid samples. In the clinical case of hyperviscosity of blood, blood becomes very sticky. Hence, as blood falls in the inlet vertical tube, a small blood droplet often tends to stick on the vertical tube wall to leave a streak of blood, which becomes the major source of error in the measurement of liquid height levels and accordingly a major source of error in the viscosity measurement. In the present invention, an inlet vertical tube is eliminated, thus eliminating stickiness as a source of error in the viscosity measurement.

In another aspect, the capillary tube viscometer described in the prior art utilizing only gravity to drive two vertical tubes in a U-shape tube is unable to measure the viscosity of viscous samples, such as yogurt, grease, slurries of suspended particles, and hyperviscous blood, among others, since gravity alone is insufficient to drive the motion of thick liquid sample through the capillary tube. Since the viscometer described in the prior art measures height variations in the inlet and outlet vertical tubes that are open-ended at the top, a piston with a dead weight or other pumping mechanism cannot be used to push the thick liquid through the capillary tube. The present invention utilizes a reservoir, i.e., like a syringe, where viscosity calculations are not based on the height change over time. Furthermore, a piston plunger with a dead weight or pumping mechanism can be used to push such a thick liquid through the capillary tube so that the viscosity of any liquid can be measured including very thick liquids.

In another aspect, the capillary tube viscometer described in the prior art utilizing only gravity to drive two vertical tubes in a U-shape tube cannot accurately measure height change as the liquid levels in the two vertical tubes never fully equilibrate. The inlet vertical tube is fully wet and the outlet vertical tube is fully dry during the course of a viscosity test, so the surface tensions of the two tubes are different. At the end of the test, the two liquid heights never become equal even at t=infinity. For example, in case of two vertical tubes each having an inner diameter of 3 mm, the height difference between the two vertical tubes is approximately 1.2 cm in the prior art (K. Kensey and Y. Cho, "Method for determining the viscosity of an adulterated blood sample over plural shear rates," 2004; K. Kensey, W. N. Hogenauer, S. Kim, and Y. Cho, "Dual riser/single capillary viscometer," 2002; S. Kim, Y. Cho, W. Hogenauer, and K. Kensey, "A method of isolating surface tension and yield stress effects in a U-shaped scanning capillary-tube viscometer using a Casson model" Journal of Non-Newtonian Fluid Mechanics, vol. 103, pp. 205-219, 2002). Since liquid height in the two vertical tubes cannot equilibrate, the surface tension of liquid cannot experimentally be determined.

The present invention utilizes a single vertical tube and a liquid reservoir so that the capillary rise in the vertical tube is experimentally measured, from which the actual surface tension of the liquid is experimentally determined and used in the calculation of the liquid viscosity. In the present invention, the surface tension σ of liquid is experimentally determined using the two measured values, $h_1(\infty)$ and $h_2(\infty)$, which is in turn used in the determination of viscosity of liquid, a critical improvement for accurate viscosity measurement, particularly for low-shear viscosity measurement. In contrast, the dual-riser single-capillary viscometer described in the prior art treats surface tension as one of the unknown constants (S. Kim, Y. Cho, W. Hogenauer, and K. Kensey, "A method of isolating surface tension and yield stress effects in a U-shaped scanning capillary-tube viscometer using a Casson model" Journal of Non-Newtonian Fluid Mechanics, vol. 103, pp. 205-219, 2002). More specifically, the prior art used a Casson model to relate the shear stress and shear rate with two unknown constants: Casson constant k and yield stress $\tau_y$. The surface tension term was then added as the third unknown constant in the Casson model analysis in the prior art, adding uncertainty to the calculation of viscosity. The present invention experimentally measures the actual surface tension of liquid, which more accurately calculates viscosity.

In another aspect, the dual-riser single-capillary viscometer described in the prior art requires liquid samples of approximately 3 mL for viscosity measurements. Since the actual volume of liquid sample in the capillary tube is only 0.05 ml in the prior art, approximately 98% of liquid sample is in the liquid introduction tube (often called the mini-volume line) outside of the U-shaped tube and the two vertical tubes in the U-shaped tube. The present invention does not utilize a liquid sample introduction tube. The exemplary embodiments depicted in FIGS. 1 and 8 utilize only one vertical tube, whereas the exemplary embodiment depicted in FIG. 13 does not use any vertical tubes. Instead, liquid samples are introduced directly to the liquid reservoirs of the devices of the present invention so that the viscosity test can be completed with a much smaller volume (i.e., 0.5 ml) than in the prior art.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A viscosity measuring device, comprising:
    a syringe fluidly connected to a valve;
    a first reservoir having a first end and a second end, the first end fluidly connected to the valve;
    a capillary tube having a first end and a second end, the first end fluidly connected to the first reservoir;
    a second reservoir having a first end and a second end, the first end fluidly connected to the second end of the capillary tube; and
    an air chamber comprising a pressure transducer, the air chamber fluidly connected to the second end of the second reservoir;
    wherein the syringe and valve are removable, and wherein a liquid sample deposited into the first reservoir can be displaced into the second reservoir by air displaced by the syringe to create a pressure in the air chamber, and wherein the pressure may be released by opening the valve.

2. The device of claim 1, wherein the syringe comprises a plunger that is at least partially lockable.

3. The device of claim 1, wherein the first reservoir, capillary tube, second reservoir, and fluid connections may be contained within a single module.

4. The device of claim 2, wherein the module is disposable.

5. A method of testing a liquid sample using the device of claim 1, comprising the steps of:
    loading a liquid sample into the first reservoir;
    attaching the syringe and the valve to the first reservoir with the syringe being at least partially drawn and the valve closed;
    applying a compression force to the syringe to displace the liquid sample into the second reservoir and to introduce a pressure into the air chamber;
    opening the valve and recording the start time point at the time of opening; and
    recording the end time point when the pressure in the air chamber reaches atmospheric pressure.

6. A method of calculating viscosity μ of a liquid sample using the device of claim 1 and the equation:

$$\mu = \left( \frac{A_c \cdot d^2}{32 \cdot L \cdot VOL_2(t)} \right) \left[ \frac{(P_2(t) - P_1 - \Delta P_{th}) \cdot P_2(t)}{\left( \frac{dP_2(t)}{dt} \right)} \right]$$

wherein
$A_c$=cross-sectional area of the capillary tube;
d=inner diameter of the capillary tube;
L=length of the capillary tube;
$VOL_2(t)$=volume of air in the air chamber;
$P_2(t)$=pressure in the air chamber; and
$P_1$=atmospheric pressure.

* * * * *